United States Patent [19]

Kozarsky et al.

[11] Patent Number: 5,962,322

[45] Date of Patent: Oct. 5, 1999

[54] METHODS FOR MODULATION OF CHOLESTEROL TRANSPORT

[75] Inventors: Karen Kozarsky, Philadelphia, Pa.; Attilio Rigotti, Malden; Monty Krieger, Needham, both of Mass.

[73] Assignees: Massachusetts Institute of Technology, Cambridge, Mass.; The Trustees of the University of Pennsylvania, Philadelphia, Pa.

[21] Appl. No.: 08/749,907

[22] Filed: Nov. 15, 1996

[51] Int. Cl.$^6$ .............................. C12N 5/06; C12N 5/10
[52] U.S. Cl. .............................. 435/375; 514/2; 514/12; 514/144; 536/23.5; 435/320.1; 435/455; 435/456; 435/458; 435/471; 435/325; 435/361; 435/235.1; 935/9; 935/32; 935/33; 935/34; 935/52; 935/57; 935/70; 935/71; 424/9.1; 424/9.2
[58] Field of Search .................... 514/2, 12, 44; 536/23.5; 435/320.1, 172.3, 235.1, 361, 325, 455, 456, 458, 471, 375; 424/93.1, 93.2; 935/9, 32, 33, 34, 52, 57, 70, 71

[56] References Cited

U.S. PATENT DOCUMENTS

| | | | |
|---|---|---|---|
| 3,625,214 | 12/1971 | Higuchi | 424/424 |
| 4,244,946 | 1/1981 | Rivier et al. | 514/15 |
| 4,305,872 | 12/1981 | Johnston et al. | 530/330 |
| 4,316,891 | 2/1982 | Guillemin et al. | 514/11 |
| 4,629,784 | 12/1986 | Stammer | 530/328 |
| 4,789,734 | 12/1988 | Pierschbacher | 530/395 |
| 4,792,525 | 12/1988 | Ruoslahti et al. | 435/402 |
| 4,868,116 | 9/1989 | Morgan et al. | 435/373 |
| 4,906,474 | 3/1990 | Langer et al. | 514/772.3 |
| 4,925,673 | 5/1990 | Steiner et al. | 424/458 |
| 4,980,286 | 12/1990 | Morgan et al. | 435/172.3 |
| 5,510,466 | 4/1996 | Kreiger et al. | 530/395 |
| 5,652,224 | 7/1997 | Wilson et al. | 514/44 |

FOREIGN PATENT DOCUMENTS

| | | |
|---|---|---|
| 3290184 | 12/1991 | Japan . |
| 519279 | 11/1993 | Japan . |
| WO 90/05748 | 5/1990 | WIPO . |
| WO 93/01286 | 1/1993 | WIPO . |
| 96/00288 | 1/1996 | WIPO . |

OTHER PUBLICATIONS

Acton et al. (1996) Science 271: 518–520.
Kozarsky et al. (1997) Nature 387: 414–417.
Ye et al. (1996) J. Biol. Chem. 271(7): 3639–3646.
Landschulz et al. (1996) J. Clin. Invest. 98: 984–995.
Abrams, John M., et al., "Macrophages in Drosophila embryos and L2 cells exhibit scavenger receptor–mediated endocytosis," Proc. Nat. Acad. USA 89:10375–10379 (1992).
Abumrad, Nada, et al., "Cloning of a Rat Adipocyte Membrane Protein Implicated in Binding or Transport of Long–chain Fatty Acids That Is Induced during Preadipocyte Differentiation," J. Biol. Chem. 268, 17665–17668 (1993).
Acton, Susan, et al., "The Collagenous Domains of Macrophage Scavenger Receptors and Complement Component C1g Mediate The Similar, But Not Identical, Binding Specificities for Polyanionic Ligands," J. Biol. Chem. 268, 3530–3537 (1993).
Acton, Susan L., et al., "Expression Cloning of SR–BI, a CD36–related Class B Scavenger Receptor," J. Biol. Chem. 269, 21003–21009 (1994).
Agrawal, Sudhir, et al., "Oligodeoxynucleoside phosphoramidates and phosphorothioates as inhibitors of human immunodeficiency virus," Proc. Natl. Acad. Sci. USA 85, 7079–7083 (1988).
Arai, Hidenori, et al., "Multiple Receptors for Modified Low Density Lipoproteins in Mouse Peritoneal Macrophages: Different Uptake Mechanisms for Acetylated and Oxidized Low Density Lipoproteins," Biochem. Biophys. Res. Commun. 159, 1375–1382 (1989).
Aruffo, Aleiandro and Brian Seed, "Molecular cloning of CD28 cDNA by a high–efficiency COS cell expression system," Proc. Natl. Acad. Sci. USA 84, 8573–8577 (1987).
Asch, Adam, et al., "Isolation of the Thrombospondin Membrane Receptor," J. Clin. Invest. 79, 1054–1061 (1987).
Ashkenas, John, et al., "Structures and high and low affinity ligand binding properties of murine type I and type II macrophage scavenger receptors," J. Lipid Res. 34, 983–1000 (1993).
Askew, Ben, et al., "Molecular Recoginition with Convergent Functional Groups, Synthetic and Structural Studies with a Model Receptor for Nucleic Acid Components", J. Am. Chem. Soc. 111, 1082–1090 (1989).
Baldini, Giulia, et al., "Cloning of a Rab3 isotype predominantly expressed in adipocytes," Proc. Natl. Acad. Sci. U.S.A. 89, 5049–5052 (1992).

(List continued on next page.)

Primary Examiner—Christopher S. F. Low
Attorney, Agent, or Firm—Arnall Golden & Gregory, LLP

[57] ABSTRACT

Methods for regulation of lipid and cholesterol uptake are described which are based on regulation of the expression or function of the SR-BI HDL receptor. The examples demonstrate that estrogen dramatically downregulates SR-BI under conditions of tremendous upregulation of the LDL-receptor. The examples also demonstrate the upregulation of SR-BI in rat adrenal membranes and other non-placental steroidogenic tissues from animals treated with estrogen, but not in other non-placental non-steroidogenic tissues, including lung, liver, and skin. Examples further demonstrate the uptake of fluorescently labeled HDL into the liver cells of animal, which does not occur when the animals are treated with estrogen. Examples also demonstrate the in vivo effects of SR-BI expression on HDL metabolism, in mice transiently overexpressing hepatic SR-BI following recombinant adenovirus infection. Overexpression of the SR-BI in the hepatic tissue caused a dramatic decrease in cholesterol blood levels. These results demonstrate that modulation of SR-BI levels, either directly or indirectly, can be used to modulate levels of cholesterol in the blood.

10 Claims, 3 Drawing Sheets

OTHER PUBLICATIONS

Basu, Sandip, et al., "Independent Pathways for Secretion of Cholesterol and Apolipoprotein E by Macrophages," *Science* 219, 871–873 (1983).

Bickel, Perry E. and Mason W. Freeman, "Rabbit Aortic Smooth Muscle Cells Express Inducible Macrophage Scavenger Receptor Messenger RNA That Is Absent from Endothelial Cells," *J. Clin. Invest.* 90, 1450–1457 (1992).

Blume et al., "Triple helix formation by purine–rich oligonucleotides targeted to the human dihydrofolate reductase promoter", *Nucl. Acids Res.* 20, 1777–1784 (1992).

Brown and Goldstein, "Lipoprotein Metabolism in the Macrophage: Implications for Cholesterol Deposition in Atherosclerosis", *Annu. Rev. Biochem.* 52, 223–261 (1983).

Charron et al., "A glucose transport protein expressed predominately in insulin–responsive tissues", *Proc. Natl. Acad. Sci. U.S.A.* 86, 2535–2539 (1989).

Chen et al., "NPXY, a Sequence Often Found in Chyoplasmic Tails, is Required for Coated Pit–mediated Internalization of the Low Density Lipoprotein Receptor", *J. Biol. Chem.* 265, 3116–3123 (1990).

Clackson, T., et al., "Making antibody fragments using phage display libraries", *Nature,* 352:624–688 (1991).

Cooney et al., "Site–Specific Oligonucleotide Binding Represses Transcription of the Human c–myc Gene in Vitro", *Science* 241, 456–459 (1988).

Crooke, "Progress toward oligonucleotide therapeutics: pharmacodynamic properties", *FASEB J.* 533–539 (1993).

Cullen, "Use of Eukaryotic Expression Technology in the Functional Analysis of Cloned Genes", *Methods in Enz.* 152:684–704 (1987).

Daugherty, et al., "Polymerase chain reaction facilitates the cloning, CDR–grafting, and rapid expression of a murine monoclonal antibody directed against the CD18 component of leukocyte integrins", *Nucl. Acids Res.,* 19:2471–2476 (1991).

Doi et al., "Charged Collagen Structure Mediates the Recognition of Negativily Charged Macromolecules by Macrophage Scavenger Receptors", *J. Biol. Chem.* 268, 2126–2133 (1993).

Duval–Valentin et al., "Specific inhibition of transcription by triple helix–forming oligonucleotides", *Proc. Natl. Acad. Sci. USA* 89, 504–508 (1992).

Ellington and Szostak, "Selection in vitro of single–stranded DNA molecules that fold into specific ligand–binding structures", *Nature* 355:850–852 (1992).

Endemann, et al., "CD36 Is a Receptor for Oxidized Low Density Lipoprotein", *J. Biol. Chem.* 268, 11811–11816 (1993).

Faust and Krieger, "Expression of Specific High Capacity Mevalonate Transport in a Chinese Hamster Ovary Cell Variant", *J. Biol. Chem.* 262, 1996–2004 (1987).

Fraser et al., "Divalent cation–independent macrophage adhesion inhibited by monoclonal antibody to murine scavenger receptor", *Nature* 364, 343–346 (1993).

Freeman et al., "Expression of type I and type II bovine scavenger receptors in Chinese hamster ovary cells: Lipid droplet accumulation and nonreciprocal cross competition by acetylated and oxidized low density lipoprotein", *Proc. Natl. Acad. Sci. U.S.A.* 88, 4931–4935 (1991).

Goldstein et al., "Binding site on macrophages that mediates uptake and degradation of acetylated low density lipoprotein, producing massive cholesterol deposition", *Proc. Natl. Acad. Sci. U.S.A.* 76, 333–337 (1979).

Goldstein et al., "Receptor–Mediated Endocytosis of Low–Density Lipoprotein in Cultured Cells", *Methods Enzymol.* 98, 241–260 (1993).

Greenwalt et al., "Membrane Glycoprotein CD36: A Review of Its Roles in Adherence, Signal Transduction, and Transfusion Medicine", *Blood* 80, 1105–1115 (1992).

Gregoriadis, G., Chapter 14: "Liposomes", *Drug Carriers in Biology and Medicine* pp. 287–341 (Academic Press, 1979).

Grigoriev et al., "A Triple Helix–forming Oligonucleotide–Intercalator Conjugate Acts as a Transcriptional Repressor via Inhibition of NF $_\kappa$B Binding to Interleukin–2 Receptor α–Regulatory Sequence", *J. Biol. Chem.* 267, 3389–3395 (1992).

Haberland et al., "Two Distinct Receptors Account for Recognition of Maleyl–Albumin in Human Monocytes during Differentiation In Vitro", *J. Clin. Inves.* 77, 681–689 (1986).

Haberland et al., "Role of the Maleyl–Albumin Receptor in Activation of Murine Peritoneal Macrophages In Vitro", *J. Immunol.* 142, 855–862 (1989).

Hart and Wilcox, "A Drosophila Gene Encoding an Epithelial Membrane Protein with Homology to CD36/LIMP II", *J. Mol. Biol.* 234, 249–253 (1993).

Herz, et al., "Surface location and high affinity for calcium of a 500–kd liver membrane protein closely related to the LDL–receptor suggest a physiological role as lipoprotein receptor", *EMBO J.* 7:4119–4127 (1988).

Holt et al., "An Oligomer Complementary to c–myc mRNA Inhibits Proliferation of HL–60 Promyelocytic Cells and Induces Differentiation", *Mol. Cell. Biol.* 8, 963–973 (1988).

Horiuchi et al., "Scavenger Function of Sinusoidal Liver Cells: Acetylated Low–densisty Lipoprotein is Endocytosed via a Route Distinct from Formaldehyde–treated Serum Albumin", *J. Biol. Chem.* 259, 53–56 (1985).

Hunt and Calderwood, "Characterization and sequence of a mouse hsp70 gene and its expression in mouse cell lines", *Gene* 87, 199–204 (1990).

Itakura et al., "Synthesis and use of synthetic oligonucleotides", in *Ann. Rev. Biochem.* 53, 323–356 (1984).

Inaba, et al., "Macrophage Colony–stimulating Factor Regulates Both Activities of Neural and Acidic Cholesteryl Ester Hydrolases in Human Monocyte–derived Macrophages", *J. Clin. Invest.* 92(2), 750–757 (1993).

Kabat, H.A., et al., Sequences of Proteins of Immunological Interest, 4th Ed. (U.S. Dept. Health and Human Services, Bethesda, MD, (1987)*.

Kingsley et al., "DNA–Mediated Transfer of a Human Gene Required for Low–Density Lipoprotein Receptor Expression and for Multiple Golgi Processing Pathways", *Mol. Cell. Biol.* 6, 2734–2737 (1986).

Kingsley and Krieger, "Receptor–mediated endocytosis of low density lipoprotein: Somatic cell mutants define multiple genes required for expression of surface–receptor activity", *Proc. Natl. Acad. Sci. USA* 81:5454–5458 (1984).

Kodama et al., "Type I macrophage scavenger receptor contains α–helical and collagen–like coiled coils", *Nature* 343, 531–535 (1990).

Krieger, "Complementation of Mutations in the LDL Pathway of Receptor–Mediated Endocytosis by Cocultivation of LDL Receptor–Defective Hamster Cell Mutants", *Cell* 33, 413–422 (1983).

Krieger, "Molecular flypaper and atherosclerosis: structure of the macrophage scavenger receptor", *Trends Biochem. Sci.* 17, 141–146 (1992).

Krieger, "Reconstitution of the Hydrophobic Core of Low–Density Lipoprotein", *Meth. Enzymol.* 128, 608–613 (1986).

Krieger and Herz, "Structures and Functions of Multiligand Lipoprotein Receptors: Macrophage Scavenger Receptors and LDL Receptor–Related Protein (LRP)", *Annu. Rev. Biochem.* 63, 601–637 (1994).

Krieger et al., "Amphotericin B selection of mutant Chinese hamster cells with defects in the receptor–mediated endocytosis of low density lipoprotein and cholesterol biosynthesis", *Proc. Natl. Acad. Sci. USA* 80, 5067–5611 (1983).

Krieger et al., "Isolation of Chinese Hamster Cell Mutants Defective in the Receptor–mediated Endocytosis of Low Density Lipoprotein", *J. Mol. Biol.* 150, 167–184 (1981).

Krieger et al., "Reconstituted Low Density Lipoprotein: A Vehicle for the Delivery of Hydrophobic Fluorescent Probes to Cells", *J. Supra. Struct.* 10, 467–478 (1979).

Lewis and Dean, "Automated site–directed drug design: the formation of molecular templates in primary structure generation", *Proc. R. Soc. Lond.* 236, 125–140 (1989).

Lowry et al. "Protein Measurement with the Folin Phenol Reagent", *J. Biol. Chem.* 193, 265–275 (1951).

Maher et al., "Inhibition of DNA Binding Proteins by Oligonucleotide–Directed Triple Helix Formation", *Science* 245, 725–730 (1989).

Matsumoto et al., "Human macrophage scavenger receptors: Primary structure, expression, and localization in atherosclerotic lesions", *Proc. Natl. Acad. Sci. USA* 87, 9133–9137 (1990).

McKinlay and Rossmann, "Rational design of antiviral agents", *Annu. Rev. Pharmacol. Toxicol.* 29, 111–122 (1989).

Merrifield, J., "Solid Phase Peptide Synthesis, I. The Synthesis of a Tetrapeptide", *J. Am. Chem. Soc.* 85, 2149–2154 (1963).

Moestrup, et al., "Distribution of the $\alpha_2$–macroglobulin receptor/low density lipoprotein receptor–related protein in human tissues", *Cell Tissue Res.* 269:375–382 (1992).

Mulligan, "The Basic Science of Gene Therapy", *Science,* 260, 926–932 (1993).

Nagelkerke et al., "In Vivo and in Vitro Uptake and Degradation of Acetylated Low Density Lipoprotein by Rat Liver Endothelial, Kupffer, and Parenchymal Cells", *J. Biol. Chem.* 258, 12221–12227 (1983).

Naito et al., "Tissue Distribution, Intracellular Localization, and In Vitro Expression of Bovine Macrophage Scavenger Receptors", *Am. J. Pathol.* 139, 1411–1423 (1991).

Narang et al., in "Chemical Synthesis of Deoxyoligonucleotides by the Modified Triester Method", *Methods Enzymol.,* 65, 610–620 (1980).

Ockenhouse et al., "Activation of Monocytes and Platelets by Monoclonal Antibodies or Malaria–infected Erythrocytes Binding to the CD36 Surface Receptor in vitro", *J. Clin. Invest.* 84, 468–475 (1989).

Offensperger et al., "In vivo inhibition of duck hepatitis B virus replication and gene expressioon by phosphorothioate modified antisense oligodeoxynucleotides", *EMBO J.* 12, 1257–1262 (1993).

Oquendo et al., "CD36 Directly Mediates Cytoadherence of *Plasmodium falciparium* Parasitized Erythrocites", *Cell* 58, 95–101 (1989).

Orson et al., "Oligonucleotide inhibition of IL2R$\alpha$ mRNA transcription by promoter region collinear triplex formation in lymphocytes", *Nucl. Acids Res.* 19, 3435–3441 (1991).

Ottnad et al., "Differentiation of binding sites on reconstituted hepatic scavenger receptors using oxidized low–density lipoprotein", *Biochem J.* 281, 745–751 (1992).

Pearson, et al., "Expression cloning of dSR–CI, a class C macrophage–specific scavenger receptor from *Drosophila melanogaster*", *Proc. Natl. Acad. Sci. USA* 92:4056–4060 (1995).

Penman et al., "The Type I and Type II Bovine Scavenger Receptors Expressed in Chinese Hamster Ovary Cells Are Trimeric Proteins with Collagenous Triple Helical Domains Comprising Noncovalently Associated Monomers and $Cys^{83}$–Disulfide–linked Dimers", *J. Biol. Chem.* 266, 23985–23993 (1991).

Perry and Davies, "The Use of 3D Modelling Databases for Identifying Structure Activity Relationships", *QSAR: Quantitative Structure–Activity Relationships in Drug Design,* pp. 189–193 (Alan R. Liss, Inc. 1989).

Pitas et al., "Uptake of Chemically Modified Low Density Lipoproteins In Vivo Is Mediated by Specific Endothelial Cells", *J. Cell. Biol.* 100, 103–117 (1985).

Postel et al., "Evidence that a triplex–forming oligodeoxyribonucleotide binds to the c–myc promoter in HeLa cells, thereby reducing c–myc mRNA levels", *Proc. Natl. Acad. Sci. USA* 88, 8227–8231 (1991).

Predescu et al., "Binding and Transcytosis of Glycoalbumin by the Microvascular Endothelium of the Murine Myocardium: Evidence that Glycoalbumin Behaves as a Bifunctional Ligand", *J. Cell Biol.* 107, 1729–1738 (1988).

Rigotti, et al., "The Class B Scavenger Receptors SR–BI and CD36 Are Receptors for Anionic Phospholipids", *J. Biol. Chem.* 270:1–4 (1995).

Ripka, "Computers picture the perfect drug", *New Scientist* 54–57 (Jun. 16, 1988).

Rohrer et al., "Coiled–coil fibrous domains mediate ligand binding by macrophage scavenger receptor type II", *Nature* 343:570–572 (1990).

Rouvinen, et al., "Computer–aided Drug Design", *Acta Pharmaceutica Fennica* 97, 159–166 (1988).

Sarin et al., "Inhibition of acquired immunodeficiency syndrome virus by oligodeoxynucleoside methylphosphonates", *Proc. Natl. Acad. Sci. USA* 85, 7448–7451 (1989).

Savill et al., "Macrophaage Vitronectin Receptor, CD36, and Thrombospondin Cooperate in Recognition of Neutrophils Undergoing Programmed Cell Death", *Chest* 99, 6S–7S (suppl) (1991).

Schaub, et al., "Recombinant Human Macrophage Colony–Stimulating Factor Reduces Plasma Cholesterol and Carrageenan Granuloma Foam Cell Formation in Watanabe Heritable Hyperlipidemic Rabbits", *Arterioscler. Thromb.* 14(1), 70–76 (1994).

Schnitzer et al. "Preferential Interaction of Albumin–binding Proteins, gp30 and gp18 with Conformationally Modified Albumins", *J. Biol. Chem.* 267, 24544–24553 (1992).

Scriver, et al., eds., in The Metabolic and Molecular Bases of Inherited Disease, vol. II, 7th Ed., pp. 2033–2034 and 2060–2061, New York: McGraw Hill.

Sege et al., "Expression and regulation of human low–density lipoprotein receptors in Chinese hamster ovary cells", *Nature* 307, 742–745 (1984).

Sege, et al., "Characterization of a Family of Gamma–Ray–Induced CHO Mutants Demonstrates that the IdlA Locus is Diploid and Encodes the Low–Density Lipoprotein Receptor", *Mol. Cell. Biol.* 6, 3268–3277 (1986).

Shaw, et al., "Modified deoxyoligonucleotides stable to exonuclease degradation in serum", *Nucleic Acids Res.* 19, 747–750 (1991).

Sparrow et al., "A Macrophage Receptor That Recognizes Oxidized Low Density Lipoprotein but Not Acetylated Low Density Lipoprotein", *J. Biol. Chem.* 264, 2599–2604 (1989).

Stanton, et al, "A Macrophage Fe Receptor for IgG Is Also a Receptor for Oxidized Low Density Lipoprotein", *J. Biol. Chem.* 267, 22446–22451 (1992).

Steinberg et al., 1989 "Beyond Cholesterol: Modifications of Low–Density Lipoprotein That Increase Its Atherogenicity", *N. Eng. J. Med.* 320, 915–924.

Stent, G.S. and R. Calender, *Molecular Genetics*, W.H. Freeman & Co., pp. 213–219 (1971).

Szostak, "In vitro genetics", *TIBS* 17:89–93, (1992).

Tandon et al., "Identification of Glycoprotein IV (CD36) as a Primary Receptor for Platelet–Collagen Adhesion", *J. Biol. Chem.* 264, 7576–7583 (1989).

VandePol, et al., Clinical Applications of Recombinant Macrophage–Colony Stimulating Factor (rhM–CSF), *Biotech. Therap.* 2:231–239 (1991).

Vega et al., 1991 "Cloning, Sequencing, and Expression of a cDNA Encoding Rat LIMP II, a Novel 74–kDa Lysosomal Membrane Protein Related to the Surface Adhesion Protein CD36", *J. Biol. Chem.* 266, 16818–16824.

Via et al., 1992 "Identification and density dependant regulation of the AC–LDL Receptor in normal and transformed bovine aortic endothelial cells (BAEC)", *The FASEB J.* 6:A371, #2135.

Villaschi et al., 1986 "Binding and Uptake of Native and Glycosylated Albumin–Gold Complexes in Perfused Rat Lungs", *Microvasc. Res.* 32, 190–199.

Wickstrom et al., 1988 "Human promyelocytic leukemia HL–60 cell proliferation and c–myc protein expression are inhibited by an antisense pentadecadeoxynucleotide targeted against c–myc mRNA", *Proc. Natl. Acad. Sci. USA* 85, 1028–1032.

Young et al., 1991 "Triple helix formation inhibits transcription elongation in vitro", *Proc. Natl. Acad. Sci. USA* 88, 10023–10026.

Zamecnik et al., 1978 "Inhibition of Rous sarcoma virus replication and cell transformation by a specific oligodeoxynucleotide", *Proc. Natl. Acad. Sci. USA* 75, 280–284.

Zamecnik et al., 1986 "Inhibition of replication and expression of human T–cell lymphotropic virus type III in cultured cells by exogenous systhenic oligonucleotides complementary to viral RNA", *Proc. Natl. Acad. Sci.*, 83, 4143–4146.

Zhu et al., 1993 "Systemic Gene Expression After Intravenous DNA Delivery into Adult Mice", *Science* 261, 209–211.

Krieger, et al., "Molecular Flypaper, Host Defense, and Atherosclerosis", J. Biol. Chem., 268:4569–4572 (1993).

Luoma, et al., "Expression of q2–Macroglobulin Receptor/Low Density Lipoprotein Receptor–Related Protein and scavenger Receptor in Human Atherosclerotic Lesion", J. Clin. Invest., 93:2014–2021 (1994).

*Anderson & Dietschy, J. Biol. Chem., 256:7362 (1981).

Rigotti, et al., "The Class B Scavenger Receptors SR–BI and CD36 Are Receptors for Anionic Phospholipids", J. Biol. Chem., 270:16221–16224 (1995).

De Rijke, et al., "Binding Characteristics of Scavenger Receptors on Liver Endothelial and Kupffer Cells for Modified Low–Density Lipoproteins", Biochem. J., 304:69–73 (1994).

Fukasawa, et al., "Chinese Hamster Ovary Cells Expressing a Novel Type of Acetylated Low Density Lipoprotein Receptor", J. Biol. Chem., 270:1921–1027 (1995).

Kobzik, "Lung Macrophage Uptake of Unopsonized Environmental Particulates", J. of Immunol., 155:367–376 (1995).

*Glass, et al., J. Biol. Chem., 260:744–750 (1985).

*Goldstein, et al., in the Matabolic and Molecular Bases of Inherited Disease, Scriver, et al (McGraw–Hill, NY 1995), pp. 1981–2030.

*Huang, et al., Proc. Natl. Acad. Sci. USA, 88:7844–7848 (1991).

*Joyner, et al., Nature, 338:153–156 (1989).

*Nestler, et al., Endocrinology, 117:502 (1985).

*Pitas, et al., Arterioclerosis, 1:177 (1981).

*Reaven, et al., J. Lipid Res., 36:1602 (1995).

Krieger, et al., "Molecular Flypaper Atherosclerosis, and Host Defense: Structure and Function of the Macrophage Scavenger Receptor", Cold Spring Harbor Symposia On Quantitative Biology, vol. LVII, The Cell Surface, 605–609 (1992).

*Chung, et al., "[8]Single Vertical Spin density Gradient Ultracentrifugation,"in Methods of Enzymology, Ed J.P. Segrest and J.J. Albers (Academic Press, Inc. Orlando, Fl 1986) vol. 128, pp. 181–209.

*Glass, et al., "Dissociation of Tissue Uptake of Cholesterol Ester From That of Apoprotein A–1 of Rat Plasma High Density Lipoprotein: Selective Delivery of Cholesterol Ester Liver, Adrenal, and Gonad, "Proc. Natl. Acad. sci. USA 80, 5435 (1983).

*Hogan, et al., Manipulating the mouse embryo, Cold Spring Harbor Laboratory, Cold Spring Harbor, NY (1986).

*Khoo, et al., "Selective Update of HDL Cholesteryl Esters is Active in Transgenic Mice Expressing Human Apolipoprotein A–1,"J. Lipid Res.,36:593 (1995).

*Pieters, et al., "In Vitro and in Vivo Evidence for the Role of HDL in Reverse Cholesterol Transport,"Biochim. Biophys. Acta,1225: 125 (1994).

*Potter, et al., "Enhancer–dependent Expression of Human $_K$Immunoglobulin Genes Introduced Into Mouse Pre–B Lymphocytes by Electroporation,"Proc. Natl. Acad. sci. USA,81:7161 (1984).

*Scriver, et al., eds., in The Metabolic and Molecular Bases of Inherited Disease, vol.,11, 7th Ed., pp. 2033–2034 and 2060–2061, New York: McGraw Hill.

*stein, et al., "Metabolic of HDI–Cholesteryl Ester in the Rat, Studied With a Nonhydrolyzable Analog, Cholesteryl linoleyl Ether,"Biochim. Biophys. Acta,752:98 (1983).

*Tall, et al., "Mechanisms of Enhancement of Cholesteryl Ester Transfer Protein Activity by Lipolysis*,"(Columbia University, sammett and Tall, *J. Biol. Chem.,*260:6687 (1985).

*Zimmer & Gruss, "Production of Chimaeric Mice Containing Embryonic Stem (ES) Cells Carrying a Homoeobox Hox 1.1 Allele Mutated by Homologous Recombination, "Nature,338:150–153 (1989).

METHODS FOR MODULATION OF CHOLESTEROL TRANSPORT

BACKGROUND OF THE INVENTION

The present invention is generally in the area of modulation of cholesterol transport via the SR-BI scavenger receptor.

The U.S. government has certain rights to this invention by virtue of Grants HL41484, HI-52212, and HL20948 from the National Institutes of Health-National Heart, Lung and Blood Institute.

The intercellular transport of lipids through the circulatory system requires the packaging of these hydrophobic molecules into water-soluble carriers, called lipoproteins, and the regulated targeting of these lipoproteins to appropriate tissues by receptor-mediated pathways. The most well characterized lipoprotein receptor is the LDL receptor, which binds to apolipoproteins B-100 (apoB-100) and E (apoE), which are constituents of low density lipoprotein (LDL), the principal cholesteryl-ester transporter in human plasma, very low-density lipoprotein (VLDL), a triglyceride-rich carrier synthesized by the liver, intermediate-density lipoprotein (IDL), and catabolized chylomicrons (dietary triglyceride-rich carriers).

All members of the LDL receptor gene family consist of the same basic structural motifs. Ligand-binding (complement-type) cysteine-rich repeats of approximately 40 amino acids are arranged in clusters (ligand-binding domains) that contain between two and eleven repeats. Ligand-binding domains are always followed by EGF-precursor homologous domains. In these domains, two EGF-like repeats are separated from a third EGF-repeat by a spacer region containing the YWTD motif. In LRP and gp330, EGF-precursor homologous domains are either followed by another ligand-binding domain or by a spacer region. The EGF-precursor homology domain, which precedes the plasma membrane, is separated from the single membrane-spanning segment either by an O-linked sugar domain (in the LDL receptor and VLDL receptor) or by one (in C. elegans and gp330) or six EGF-repeats (in LRP). The cytoplasmic tails contain between one and three "NPXY" internalization signals required for clustering of the receptors in coated pits. In a later compartment of the secretory pathway, LRP is cleaved within the eighth EGF-precursor homology domain. The two subunits LRP-515 and LRP-85 (indicated by the brackets) remain tightly and non-covalently associated. Only partial amino acid sequence of the vitellogenin receptor and of gp330 are available.

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors type I and type II.

Scavenger receptors mediate the endocytosis of chemically modified lipoproteins, such as acetylated LDL (AcLDL) and oxidized LDL (OxLDL), and have been implicated in the pathogenesis of atherosclerosis (Krieger and Herz, 1994 *Annu. Rev. Biochem.* 63, 601–637; Brown and Goldstein, 1983 *Annu. Rev. Biochem.* 52, 223–261; Steinberg et al., 1989 *N. Enql. J. Med.* 320, 915–924). Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 *Proc. Natl. Acad. Sci. U.S.A.* 88, 4931–4935, Krieger and Herz, 1994). Several investigators have suggested that there may be at least three different classes of such receptors expressed on mammalian macrophages, including receptors which recognize either AcLDL or OxLDL, or both of these ligands (Sparrow et al., 1989 *J. Biol. Chem.* 264, 2599–2604; Arai et al., 1989 *Biochem. Biophys. Res. Commun.* 159, 1375–1382; Nagelkerke et al., 1983 *J. Biol. Chem.* 258, 12221–12227).

The first macrophage scavenger receptors to be purified and cloned were the mammalian type I and II receptors. These are trimeric integral membrane glycoproteins whose extracellular domains have been predicted to include a-helical coiled-coil, collagenous and globular structures (Kodama et al., 1990 *Nature* 343, 531–535; Rohrer et al., 1990 *Nature* 343, 570–572; Krieger and Herz, 1994). The collagenous domain, shared by the type I and type II receptors, apparently mediates the binding of polyanionic ligands (Acton et al., 1993 *J. Biol. Chem.* 268, 3530–3537; Doi et al., 1993 *J. Biol. Chem.* 268, 2126–2133). The type I and type II molecules, which are the products of alternative splicing of a single gene, are hereafter designated class A scavenger receptors (SR-AI and SR-AII). The class A receptors, which bind both AcLDL and OxLDL (Freeman et al., 1991), have been proposed to be involved in host defense and cell adhesion, as well as atherogenesis (Freeman et al., 1991; Krieger, 1992 *Trends Biochem. Sci.* 17, 141–146; Fraser et al., 1993 *Nature* 364, 343–346; Krieger and Herz, 1994).

Based on models of the predicted quaternary structures of the type I and type II macrophage scavenger receptors, both contain six domains, of which the first five are identical: the N-terminal cytoplasmic region, the transmembrane region, spacer, α-helical coil, and collagen-like domains. The C-terminal sixth domain of the type I receptor is composed of an eight-residue spacer followed by a 102-amino acid cysteine-rich domain (SRCR), while the sixth domain of the type II receptor is only a short oligopeptide.

Using a murine macrophage cDNA library and a COS cell expression cloning technique, Endemann, Stanton and colleagues, (Endemann, et al. 1993 *J. Biol. Chem.* 268, 11811–11816; Stanton, et al. *J. Biol. Chem.* 267, 22446–22451), reported the cloning of cDNAs encoding two additional proteins that can bind OxLDL. The binding of OxLDL to these proteins was not inhibited by AcLDL. These proteins are FcgRII-B2 (an Fc receptor) (Stanton et al., 1992) and CD36 (Endemann et al., 1993). The significance of the binding of OxLDL to FcgRII-B2 in transfected COS cells is unclear because FcgRII-B2 in macrophages apparently does not contribute significantly to OxLDL binding (Stanton et al., 1992). However, CD36 may play a quantitatively significant role in OxLDL binding by macrophages (Endemann et al., 1993). In addition to binding oxidized LDL, CD36 binds thrombospondin (Asch et al., 1987 *J. Clin. Invest.* 79, 1054–1061), collagen (Tandon et al., 1989 *J. Biol. Chem.* 264, 7576–7583), long-chain fatty acids (Abumrad et al., 1993 *J. Biol. Chem.* 268, 17665–17668) and *Plasmodium falciparum* infected erythrocytes (Oquendo et al., 1989 *Cell* 58, 95–101). CD36 is expressed in a variety of tissues, including adipose, and in macrophages, epithelial cells, monocytes, endothelial cells, platelets, and a wide variety of cultured lines (Abumrad et al., 1993; and see Greenwalt et al., 1992 *Blood* 80, 1105–1115 for review). Although the physiologic functions of CD36 are not known, it may serve as an adhesion molecule due to its collagen-binding properties. It is also been proposed to be a long-chain fatty acid transporter (Abumrad et al., 1993) and a signal transduction molecule (Ockenhouse et al., 1989 *J. Clin. Invest.* 84, 468–475; Huang et al., 1991 *Proc. Natl. Acad. Sci. USA* 88, 7844–7848), and may serve as a receptor on macrophages for senescent neutrophils (Savill et al., 1991 *Chest* 99, 7 (suppl)).

Modified lipoprotein scavenger receptor activity has also been observed in endothelial cells (Arai et al., 1989; Nagelkerke et al., 1983; Brown and Goldstein, 1983; Goldstein et al., 1979 *Proc. Natl. Acad. Sci. U.S.A.* 76, 333–337). At least some of the endothelial cell activity apparently is not mediated by the class A scavenger receptors (Bickel et al., 1992 *J. Clin. Invest.* 90, 1450–1457; Arai et al., 1989; Nagelkerke et al., 1983; Via et al., 1992 *The Faseb J.* 6, A371), which are often expressed by macrophages (Naito et al., 1991 *Am. J. Pathol.* 139, 1411–1423; Krieger and Herz, 1994). In vivo and in vitro studies suggest that there may be scavenger receptor genes expressed in endothelial cells and macrophages which differ from both the class A scavenger receptors and CD36 (Haberland et al., 1986 *J. Clin. Inves.* 77, 681–689; Via et al., 1992; Sparrow et al., 1989; Horiuchi et al., 1985 *J. Biol. Chem.* 259, 53–56; Arai et al., 1989; and see below). Via, Dressel and colleagues (Ottnad et al., 1992 *Biochem J.* 281, 745–751) and Schnitzer et al. 1992 *J. Biol. Chem.* 267, 24544–24553) have detected scavenger receptor-like binding by relatively small membrane associated proteins of 15–86 kD. In addition, the LDL receptor related protein (LRP) has been shown to bind lipoprotein remnant particles and a wide variety of other macromolecules. Both the mRNA encoding LRP and the LRP protein are found in many tissues and cell types (Herz, et al., 1988 *EMBO J.* 7:4119–4127; Moestrup, et al., 1992 *Cell Tissue Res.* 269:375–382), primarily the liver, the brain and the placenta. The predicted protein sequence of the LRP consists of a series of distinctive domains or structural motifs, which are also found in the LDL receptor.

As described by Kreiger, et al., in PCT/US95/07721 "Class BI and CI Scavenger Receptors" Massachusetts Institute of Technology ("Krieger, et al."), two distinct scavenger receptor type proteins having high affinity for modified lipoproteins and other ligands have been isolated, characterized and cloned. Hamster and murine homologs of SR-BI, an AcLDL and LDL binding scavenger receptor, which is distinct from the type I and type II macrophage scavenger receptors, has been isolated and characterized. In addition, DNA encoding the receptor cloned from a variant of Chinese Hamster Ovary Cells, designated Var-261, has been isolated and cloned. dSR-CI, a non-mammalian AcLDL binding scavenger receptor having high ligand affinity and broad specificity, was isolated from *Drosophila melanogaster*.

It was reported by Kreiger, et al. that the SR-BI receptor is expressed principally in steroidogenic tissues and liver and appears to mediate HDL-transfer and uptake of cholesterol. Competitive binding studies show that SR-BI binds LDL, modified LDL, negatively charged phospholipid, and HDL. Direct binding studies show that SR-BI expressed in mammalian cells (for example, a varient of CHO cells) binds HDL, without cellular degradation of the HDL-apoprotein, and lipid is accumulated within cells expressing the receptor. These studies indicate that SR-BI might play a major role in transfer of cholesterol from peripheral tissues, via HDL, into the liver and steroidogenic tissues, and that increased or decreased expression in the liver or other tissues may be useful in regulating uptake of cholesterol by cells expressing SR-BI, thereby decreasing levels in foam cells and deposition at sites involved in atherogenesis.

Atherosclerosis is the leading cause of death in western industrialized countries. The risk of developing atherosclerosis is directly related to plasma levels of LDL cholesterol and inversely related to HDL cholesterol levels. Over 20 years ago, the pivotal role of the LDL receptor in LDL metabolism was elucidated by Goldstein, et al., in the Metabolic and Molecular Bases of Inherited Disease, Scriver, et al. (McGraw-Hill, NY 1995), pp. 1981–2030. In contrast, the cellular mechanisms responsible for HDL metabolism are still not well defined. It is generally accepted that HDL is involved in the transport of cholesterol from extrahepatic tissues to the liver, a process known as reverse cholesterol transport, as described by Pieters, et al., *Biochim. Biophys. Acta* 1225, 125 (1994), and mediates the transport of cholesteryl ester to steroidogenic tissues for hormone synthesis, as described by Andersen and Dietschy, *J. Biol. Chem.* 256, 7362 (1981). The mechanism by which HDL cholesterol is delivered to target cells differs from that of LDL. The receptor-mediated metabolism of LDL has been thoroughly described and involves cellular uptake and degradation of the entire particle. In contrast, the receptor-mediated HDL metabolism has not been understood as well. Unlike LDL, the protein components of HDL are not degraded in the process of transporting cholesterol to cells. Despite numerous attempts by many investigators, the cell-surface protein(s) that participate in the delivery of cholesterol from HDL to cells had not been identified before the discovery that SR-BI was an HDL receptor.

It is an object of the present invention to provide methods and reagents for designing drugs that can stimulate or inhibit the binding to and lipid movements mediated by SR-BI and redirect uptake and metabolism of lipids and cholesterol by cells.

SUMMARY OF THE INVENTION

Methods for regulation of cholesterol transport are described which are based on regulation of the expression or function of the SR-BI HDL receptor.

The examples demonstrate that estrogen dramatically downregulates SR-BI under conditions of tremendous upregulation of the LDL-receptor. The examples also demonstrate the upregulation of SR-BI in rat adrenal membranes and other non-placental steroidogenic tissues from animals treated with estrogen, but not in other non-placental non-steroidogenic tissues, including lung, liver, and skin. Examples also demonstrate the in vivo effects of SR-BI expression on HDL metabolism, in mice transiently over-expressing hepatic SR-BI following recombinant adenovirus infection. Overexpression of the SR-BI in the hepatic tissue caused a dramatic decrease in blood cholesterol levels. These results demonstrate that modulation of SR-BI levels, either directly or indirectly, can be used to modulate levels of cholesterol in the blood.

DETAILED DESCRIPTION OF THE INVENTION

Figure 1A:
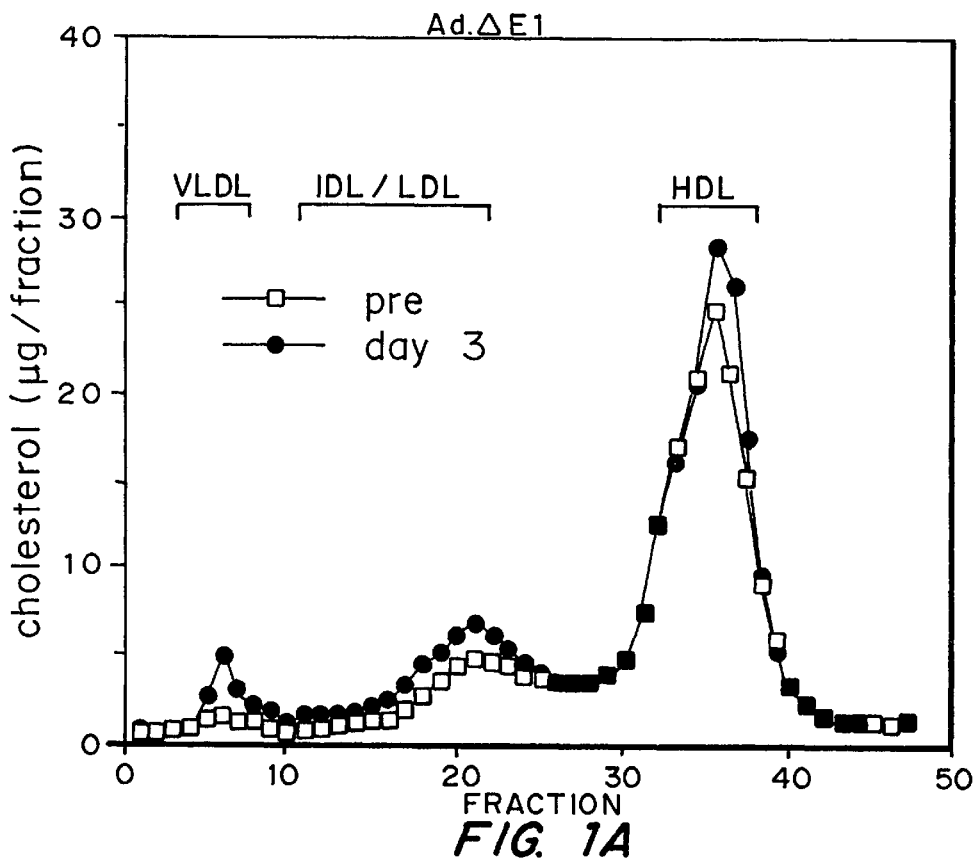
FIGS. 1A–D are graphs of fast pressure liquid chromatography (FPLC) analysis of plasma showing the lipoprotein profile of control (Ad.ΔE1) (FIGS. 1A and 1C) and transgenic mice (Ad.SR-BI) (FIGS. 1B and 1D), and cholesterol levels (micrograms/fraction) over the course of zero to three days (FIGS. 1A and 1B) and seven to twenty-one days (FIGS. 1C and 1D).

In previous studies, Western blotting was used to show that upon estrogen treatment in rats levels of SR-BI protein drop dramatically and LDL receptor levels increase in liver. As used herein, steroidogenic tissues refer to non-placental steroidogenic tissues including adrenal, ovary and testes. The liver and non-hepatic steroidogenic tissues had previously been shown to be sites of selective cholesterol uptake from HDL. Fluorescently labeled HDL has been used as a marker of lipid uptake and injected into estrogen and control treated animals. In control animals, there was a significant fluorescence in liver tissue, which was totally absent in estrogen treated animals. Given that estrogen is known to cause levels of HDL to increase in humans over time and to decrease the risk of atherosclerosis and given the evidence that changes in levels of SR-BI follow estrogen administration, one could inhibit SR-BI expression in liver by administration of estrogen, thereby decreasing the risk of atherosclerosis, although this is not preferred since estrogen also has side effects. Inhibition is more preferably achieved through the use of agents which inhibit expression of SR-BI, translation of SR-BI, binding of SR-BI, or cellular processing mediated by the SR-BI. Inhibition can be direct or indirect, competitive or irreversible.

I. Inhibitors of SR-BI Transport of Cholesterol

Direct inhibitors include nucleotide molecules such as antisense oligonucleotides, ribozymes, and triplex forming oligonucleotides which bind to the SR-BI gene, either the protein encoding region of the gene or the regulatory regions of the gene; small organic molecules which bind to the SR-BI protein; soluble SR-BI protein or fragments thereof which competitively bind to the substrate for cell bound SR-BI; and compounds which block binding of HDL to SR-BI.

In a preferred embodiment, these compounds are initially screened using an assay such as the assays described below and then tested in transgenic animals made using standard transgenic animal technology to knockout or overexpress the SR-BI gene. Since homozygous knockouts may be lethal, a technique such as embryonic stem cell technology using rats, mice or hamsters or the use of retroviral or adenoviral vectors is preferred, to yield animals expressing some SR-BI.

The cDNA encoding SR-BI has been cloned and is reported in Krieger, et al. The cDNA encoding SR-BI yields a predicted protein sequence of 509 amino acids which is approximately 30% identical to those of the three previously identified CD36 family members. The cloned hamster SR-BI cDNA is approximately 2.9 kb long. The sequences of the 5' untranslated region, the coding region, and a portion of the 3' untranslated region are shown in Sequence Listing ID No. 1. The predicted protein sequence is 509 amino acids (Sequence Listing ID No. 2) with a calculated molecular weight of 57 kD. The murine cDNA is shown in Sequence Listing ID No. 3 and the predicted amino acid sequence is shown in Sequence Listing ID No. 4.

As used herein, unless specifically stated otherwise, the term "SR-BI" refers to the nucleotide and amino acid sequences, respectively, shown in Sequence ID Nos. 1 and 2, and 3 and 4, and degenerate variants thereof and their equivalents in other species of origin, especially human, as well as functionally equivalent variants, having additions, deletions, and substitutions of either nucleotides or amino acids which do not significantly alter the functional activity of the protein as a receptor characterized by the binding activity identified above.

II. Methods of Regulation of SR-BI Cholesterol Transport

It has now been demonstrated that SR-BI and the related SR-B proteins may play critical roles in HDL lipid metabolism and cholesterol transport. SR-BI appears to be responsible for cholesterol delivery to steroidogenic tissues and liver, and actually transfers cholesterol from HDL particles through the liver cells and into the bile canniculi, where it is passed out into the intestine. Data indicates that SR-BI is also expressed in the intestinal mucosa although the location and amount appears to be correlated with stages of development. It would be useful to increase expression of SR-BI in cells in which uptake of cholesterol can be increased, freeing HDL to serve as a means for removal of cholesterol from storage cells such as foam cells where it can play a role in atherogenesis.

As discussed above, the SR-BI proteins and antibodies and their DNAs can be used in screening of drugs which modulate the activity and/or the expression of SR-BI. These drugs should be useful in treating or preventing atherosclerosis, fat uptake by adipocytes, and some types of endocrine disorders.

Nucleotide Molecules

Preferred uses for the nucleotide sequences shown in the Sequence Listings below, are for the screening of drugs altering binding of or endocytosis of ligand by the scavenger receptor proteins, or expression or translation of the SR-BI protein.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Screening for Drugs Modifying or Altering the Extent of Receptor Function or Expression The receptor proteins are useful as targets for compounds which turn on, or off, or otherwise regulate binding to these receptors. The assays described below clearly provide routine methodology by which a compound can be tested for an inhibitory effect on binding of a specific compound, such as a radiolabeled modified HDL and LDL or polyion. The in vitro studies of compounds which appear to inhibit binding selectively to the receptors are then confirmed by animal testing. Since the molecules are so highly evolutionarily conserved, it is possible to conduct studies in laboratory animals such as mice to predict the effects in humans.

Studies based on inhibition of binding are predictive for indirect effects of alteration of receptor binding. For example, inhibition of cholesterol-HDL binding to the SR-BI receptor leads to decreased uptake by cells of cholesterol and therefore inhibits cholesterol transport by cells expressing the SR-BI receptor. Increasing cholesterol-HDL binding to cells increases removal of lipids from the blood stream and thereby decreases lipid deposition within the blood stream. Studies have been conducted using a stimulator to enhance macrophage uptake of cholesterol and thereby treat atherogenesis, using M-CSF (Schaub, et al., 1994 *Arterioscler. Thromb.* 14 (1), 70–76; Inaba, et al., 1993 *J. Clin. Invest.* 92 (2), 750–757).

The following assays can be used to screen for compounds which are effective in methods for alter SR-BI expression, concentration, or transport of cholesterol.

Assays for Alterations in SR-BI Binding or Expression

Northern blot analysis of murine tissues shows that SR-BI is most abundantly expressed in adrenal, ovary, liver, testes, and fat and is present at lower levels in some other tissues. SR-BI mRNA expression is induced upon differentiation of 3T3-L1 cells into adipocytes. Both SR-BI and CD36G display high affinity binding for acetylated LDL with an apparent dissociation constant in the range of approximately 5 μg protein/ml. The ligand binding specificities of CD36G and SR-BI, determined by competition assays, are similar, but not identical: both bind modified proteins (acetylated LDL, maleylated BSA), but not the broad array of other polyanions (e.g. fucoidin, polyinosinic acid, polyguanosinic acid) which are ligands of the class A receptors. SR-BI displays high affinity and saturable binding of HDL which is not accompanied by cellular degradation of the HDL. HDL inhibits binding of AcLDL to CD36, suggesting that it binds HDL, similarly to SR-BI. Native LDL, which does not compete for the binding of acetylated LDL to either class A receptors or CD36, competes for binding to SR-BI.

$^{125}$I-AcLDL Binding, Uptake and Degradation Assays

Scavenger receptor activities at 370° C. are measured by ligand binding, uptake and degradation assays as described by Krieger, *Cell* 33, 413–422, 1983; and Freeman et al., 1991). The values for binding and uptake are combined and are presented as binding plus uptake observed after a 5 hour incubation and are expressed as ng of $^{125}$I-AcLDL protein per 5 hr per mg cell protein. Degradation activity is expressed as ng of $^{125}$I-AcLDL protein degraded in 5 hours per mg of cell protein. The specific, high affinity values represent the differences between the results obtained in the presence (single determinations) and absence (duplicate determinations) of excess unlabeled competing ligand. Cell surface 4° C. binding is assayed using either method A or method B as indicated. In method A, cells are prechilled on ice for 15 min, re-fed with $^{125}$I-AcLDL in ice-cold medium B supplemented with 10% (v/v) fetal bovine serum, with or without 75–200 μg/ml unlabeled M-BSA, and incubated 2 hr at 4° C. on a shaker. Cells are then washed rapidly three times with Tris wash buffer (50 mM Tris-HCl, 0.15 M NaCl, pH 7.4) containing 2 mg/ml BSA, followed by two 5 min washes, and two rapid washes with Tris wash buffer without BSA. The cells are solubilized in 1 ml of 0.1 N NaOH for 20 min at room temperature on a shaker, 30 μl are removed for protein determination, and the radioactivity in the remainder is determined using a LKB gamma counter. Method B differs from method A in that the cells are prechilled for 45 minutes, the medium contains 10 mM HEPES and 5% (v/v) human lipoprotein-deficient serum rather than fetal bovine serum, and the cell-associated radioactivity released by treatment with dextran sulfate is measured as described by Krieger, 1983; Freeman et al., 1991).

Northern Blot Analysis 0.5 micrograms of poly(A)+RNA prepared from different murine tissues or from 3T3-L1 cells on zero, two, four, six or eight days after initiation of differentiation into adipocytes as described by Baldini et al., 1992 *Proc. Natl. Acad. Sci. U.S.A.* 89, 5049–5052, is fractionated on a formaldehyde/agarose gel (1.0%) and then blotted and fixed onto a Biotrans™ nylon membrane. The blots are hybridized with probes that are $^{32}$P-labeled ($2\times10^6$ dpm/ml, random-primed labeling system). The hybridization and washing conditions, at 42° C. and 50° C., respectively, are performed as described by Charron et al., 1989 *Proc. Natl. Acad. Sci. U.S.A.* 86, 2535–2539. The probe for SR-BI mRNA analysis was a 0.6 kb BamHI fragment from the cDNAs coding region. The coding region of murine cytosolic hsp70gene (Hunt and Calderwood, 1990 *Gene* 87, 199–204) is used as a control probe for equal mRNA loading.

SR-BI protein in tissues is detected by blotting with polyclonal antibodies to SR-BI.

HDL Binding Studies

HDL and VLDL binding to SR-BI and CD36 are conducted as described for LDL and modified LDL.

Studies conducted to determine if the HDL which is bound to SR-BI is degraded or recycled and if lipid which is bound to the HDL is transferred into the cells are conducted using fluorescent lipid-labeled HDL, $^3$H-cholesteryl ester labeled HDL and $^{125}$I-HDL added to cultures of transfected or untransfected cells at a single concentration (10 μg protein/ml). HDL associated with the cells is measured over time. A steady state is reached in approximately thirty minutes to one hour. A fluorescent ligand, DiI, or $^3$H-cholesterol ester is used as a marker for lipid (for example, cholesterol or cholesterol ester) uptake by the cell. Increasing concentration of DiI indicates that lipid is being transferred from the HDL to the receptor, then being internalized by the cell. The DiI-depleted HDL is then released and replaced by another HDL molecule.

HDL Binding to SR-BI

Competition binding studies demonstrate that HDL and VLDL (400 μg/ml) competitively inhibit binding of $^{125}$I-AcLDL to SR-BI. Direct binding of $^{125}$I-HDL to cells expressing SR-BI is also determined.

Tissue Distribution of SR-BI

To explore the physiological functions of SR-BI, the tissue distribution of SR-BI was determined in murine tissues, both in control animals and estrogen treated animals, as described in the following examples. Each lane is loaded with 0.5 μg of poly(A)+RNA prepared from various murine tissues: kidney, liver, adrenals, ovaries, brain, testis, fat, diaphragm, heart, lung, spleen, or other tissue. The blots are hybridized with a 750 base pair fragment of the coding region of SR-BI. SR-BI mRNA is most highly expressed in adrenals, ovary and liver is moderately or highly expressed in fat depended on the source and is expressed at lower levels in other tissues. Blots using polyclonal antibodies to a cytoplasmic region of SR-BI demonstrate that very high levels of protein are present in liver, adrenal tissues, and ovary in mice and rats, but only very low or undetectable levels are present in either white or brown fat, muscle or a variety of other tissues. Bands in the rat tissues were present at approximately 82 kD. In the mouse tissues, the 82 kD form observed in the liver and steroidogenic tissues is the same size observed in SR-BI-transfected cultured cells.

Assays for testing compounds for useful activity can be based solely on interaction with the receptor protein, preferably expressed on the surface of transfected cells such as those described above, although proteins in solution or immobilized on inert substrates can also be utilized, where the indication is inhibition or increase in binding of lipoproteins.

Alternatively, the assays can be based on interaction with the gene sequence encoding the receptor protein, preferably the regulatory sequences directing expression of the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor activity in transfected or naturally occurring cells which express the receptor, then in vivo in laboratory animals. Typically, the antisense would inhibit expression. However, sequences which block those sequences which "turn off" synthesis can also be targeted.

The receptor protein for study can be isolated from either naturally occurring cells or cells which have been genetically engineered to express the receptor, as described in the examples above. In the preferred embodiment, the cells would have been engineered using the intact gene.

Random Generation of Receptor or Receptor Encoding Sequence Binding Molecules

Molecules with a given function, catalytic or ligand-binding, can be selected for from a complex mixture of random molecules in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, *OSAR: Quantitative Structure-Activity Relationships in Drug Design* pp. 189–193 (Alan R. Liss, Inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding and therefore cholesterol transport, one could also screen libraries of known compounds, including natural products or synthetic chemicals, and biologically active materials, including proteins, for compounds which are inhibitors or activators.

Generation of Nucleic Acid Regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, 1993 *Science,* 260, 926–932; U.S. Pat. No. 4,980,286; U.S. Pat. No. 4,868,116; incorporated herein by reference). For example, a delivery system in which nucleic acid is encapsulated in cationic liposomes which can be injected intravenously into a mammal has been used to introduce DNA into the cells of multiple tissues of adult mice, including endothelium and bone marrow (see, e.g., Zhu et al., 1993 *Science* 261, 209–211; incorporated herein by reference).

The 5' flanking sequences of the receptor gene can also be used to inhibit the expression of the receptor. For example, an antisense RNA of all or a portion of the 5' flanking region of the receptor gene can be used to inhibit expression of the receptor in vivo. Expression vectors (e.g., retroviral or adenoviral expression vectors) are already in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the receptor gene can be inserted into an appropriate expression vector so that upon passage into the cell, the transcription of the inserted DNA yields an antisense RNA that is complementary to the mRNA transcript of the receptor protein gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the receptor protein gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci.,* 83, 4143–4146; Wickstrom et al., 1988 *Proc. Natl. Acad. Sci. USA* 85, 1028–1032; Crooke, 1993 *FASEB J.* 7, 533–539. Furthermore, recent work has shown that improved inhibition of expression of a gene by antisense oligonucleotides is possible if the antisense oligonucleotides contain modified nucleotides (see, e.g., Offensperger et. al., 1993 *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 *Nucleic Acids Res* 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725–730; Orson et al., 1991 *Nucl. Acids Res.* 19, 3435–3441; Postal et al., 1991 *Proc. Natl. Acad. Sci. USA* 88, 8227–8231; Cooney et al., 1988 *Science* 241, 456–459; Young et al., 1991 *Proc. Natl. Acad. Sci. USA* 88, 10023–10026; Duval-Valentin et al., 1992 *Proc. Natl. Acad. Sci. USA* 89, 504–508; 1992 Blume et al., *Nucl. Acids Res.* 20, 1777–1784; 1992 Grigoriev et al., *J. Biol. Chem.* 267, 3389–3395.

Both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 *Mol. Cell. Biol.* 8, 963–973; Wickstrom et al., 1988 *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620 (1980) (phosphotriester method). Accordingly, DNA sequences of the 5' flanking region of the receptor protein gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a receptor protein gene in order to inhibit expression of the gene.

In some cases it may be advantageous to insert enhancers or multiple copies of the regulatory sequences into an expression system to facilitate screening of methods and reagents for manipulation of expression.

Preparation of Receptor Protein Fragments

Compounds which are effective for blocking binding of the receptor to the cholesterol-HDL can also consist of fragments of the receptor proteins, expressed recombinantly and cleaved by enzymatic digest or expressed from a sequence encoding a peptide of less than the full length receptor protein. These will typically be soluble proteins, i.e., not including the transmembrane and cytoplasmic regions, although smaller portions determined in the assays described above to inhibit or compete for binding to the receptor proteins can also be utilized. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking receptor binding, the $IC_{50}$, the dose of peptide required to inhibit binding by 50%, ranges from about 50 $\mu$M to about 300 $\mu$M, depending on the peptides. These ranges are well within the effective concentrations for the in vivo administration of peptides, based on comparison with the RGD-containing peptides, described, for example, in U.S. Pat. No. 4,792,525 to Ruoslahti, et al., used in vivo to alter cell attachment and phagocytosis.

The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of the receptor proteins, or, preferably, by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. No. 4,305,872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used.

These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 µg/kg of body weight. Based on extrapolation from other proteins for treatment of most inflammatory disorders, the dosage range will be between 0.1 to 70 mg/kg of body weight. This dosage will be dependent, in part, on whether one or more peptides are administered.

Pharmaceutical Compositions

Compounds which alter receptor protein binding are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. No. 4,906,474, 4,925,673, and 3,625,214.

Generation of Transgenic Animals for Screening With the knowledge of the cDNA encoding SR-BI and regulatory sequences regulating expression thereof, it is possible to generate transgenic animals, especially rodents, for testing the compounds which can alter SR-BI expression, translation or function in a desired manner. This procedure for transient overexpression in animals following infection with adenoviral vectors is described below in the examples.

There are basically two types of animals which are useful: those not expressing functional SR-BI, which are useful for testing of drugs which may work better in combination with an inhibitor of SR-BI to control levels of lipid, cholesterol, lipoprotein or components thereof, and those which overexpress SR-BI, either in those tissues which already express the protein or in those tissues where only low levels are naturally expressed.

The animals in the first group are preferably made using techniques that result in "knocking out" of the gene for SR-BI, although in the preferred case this will be incomplete, either only in certain tissues, or only to a reduced amount. These animals are preferably made using a construct that includes complementary nucleotide sequence to the SR-BI gene, but does not encode functional SR-BI, and is most preferably used with embryonic stem cells to create chimeras. Animals which are heterozygous for the defective gene can also be obtained by breeding a homozygote normal with an animal which is defective in production of SR-BI.

The animals in the second group are preferably made using a construct that includes a tissue specific promoter, of which many are available and described in the literature, or an unregulated promoter or one which is modified to increase expression as compared with the native promoter. The regulatory sequences for the SR-BI gene can be obtained using standard techniques based on screening of an appropriate library with the cDNA encoding SR-BI. These animals are most preferably made using standard microinjection techniques.

These manipulations are performed by insertion of cDNA or genomic DNA into the embryo using microinjection or other techniques known to those skilled in the art such as electroporation, as described below. The DNA is selected on the basis of the purpose for which it is intended: to inactivate the gene encoding an SR-BI or to overexpress or express in a different tissue the gene encoding SR-BI. The SR-BI encoding gene can be modified by homologous recombination with a DNA for a defective SR-BI, such as one containing within the coding sequence an antibiotic marker, which can then be used for selection purposes.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95 air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods Introduction of cDNA into ES cells

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach,* ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the SR-BI gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach,* ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid sequence and 1 mg of pSV2neo DNA (Southern and Berg, *J. Mol. Appl. Gen.* 1:327–341 (1982)) precipitated in the presence of 50 mg lipofectin in a final volume of 100 $\mu$l. The cells are fed with selection medium containing 10% fetal bovine serum in DMEM supplemented with an antibiotic such as G418 (between 200 and 500 $\mu$g/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES Cell Injection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 $\mu$m.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

The present invention will be further understood by reference to the following non-limiting examples.

EXAMPLE 1

Depletion of Blood Cholesterol Levels in Animals Transiently Overexpressing SR-BI The in vivo effects of murine SR-BI (mSR-BI) on HDL and biliary cholesterol metabolism were studied in C57BL/6 mice that transiently overexpressed hepatic mSR-BI because of infection by intravenous infusion with a recombinant, replication defective adenovirus (Ad.mSR-BI). In the Ad.mSR-BI virus, the mSR-BI cDNA is under the control of the cytomegalovirus (CMV) immediate early enhancer/promotor. Controls included mice infected with a replication defective adenovirus lacking a cDNA transgene (Ad.ΔE1 exhibited modest levels of SR-BI expression, as determined by immunofluorescence microscopy and by immunoblotting. Three days post-infection, mSR-BI expression was dramatically increased in the livers of Ad.mSR-BI treated animals. Although the amount of mSR-BI protein decreased with time after infection, levels substantially above those of controls 21 days after infection were routinely observed. Much of the increase in mSR-BI expression appeared to be localized to the apical surfaces of the hepatocytes, with especially strong focal intensities suggesting high expression in the bile canaliculi. Sinusoidal staining was also observed.

The effects of hepatic SR-BI overexpression on plasma cholesterol levels are shown in Table 1. Infusion of control adenovirus had little or no effect on total cholesterol. In contrast, infusion of Ad.SR-BI resulted in dramatic decrease in plasma cholesterol by day 3, to approx. 14% of control levels. By day 7, cholesterol levels had increased to above preinfusion levels, and returned to baseline by day 21. Plasma levels of apoAI, the major protein component of HDL, mirrored total cholesterol levels in the initial decrease observed on day 3 (Table 1); in contrast, at later time points, apoAI levels increased but did not recover to pre-infusion levels until day 21.

TABLE 1

Plasma cholesterol and apoAI levels.

| Day | Cholesterol (mg/dL) | | apoAI (mg/dL) | |
| --- | --- | --- | --- | --- |
| | Ad.ΔE1 | Ad.SR-BI | Ad.ΔE1 | Ad.SR-BI |
| pre | 131.0 | 117.8 | 33.2 | 32.6 |
| 3 | 125.5 | 16.5 | 31.0 | 5.0 |
| 7 | 146.0 | 173.0 | 33.5 | 23.4 |
| 14 | 129.0 | 152.0 | 32.5 | 26.0 |
| 21 | 113.0 | 87.5 | 34.0 | 32.0 |

The numbers shown in the above table are averages for 2 to 8 mice/time point.

Figure 1B:
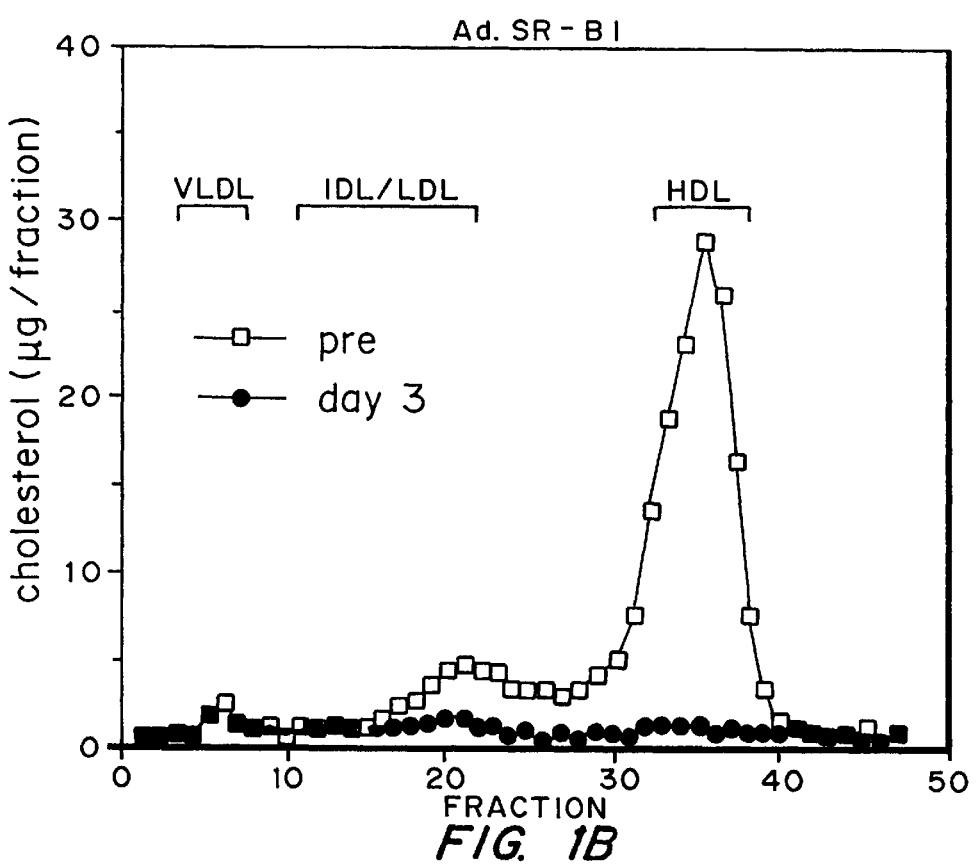
Figure 1C:
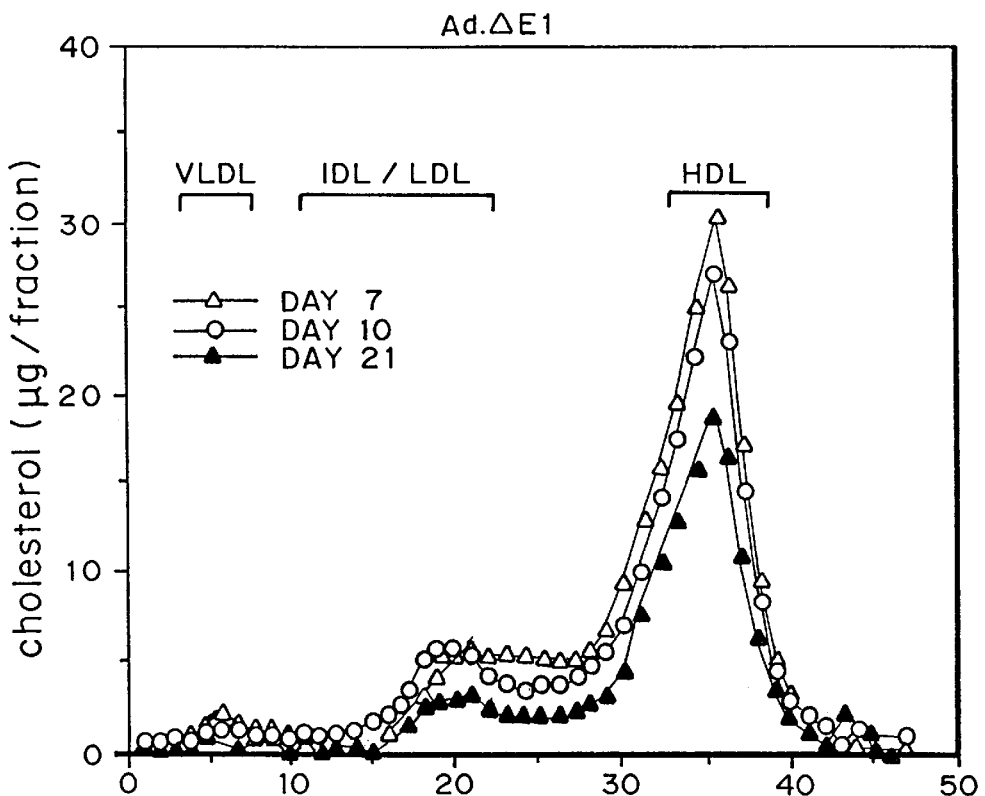
Figure 1D:
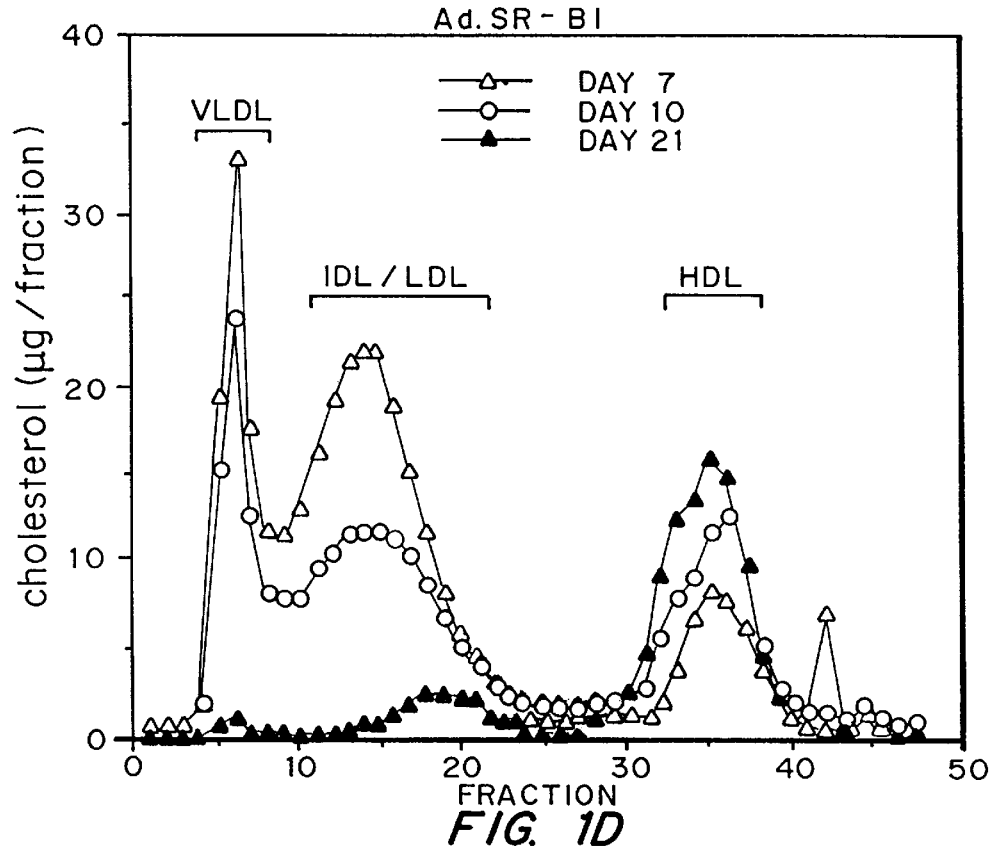

Fast pressure liquid chromatography (FPLC) analysis of plasma was performed to determine specifically the effects of hepatic SR-BI overexpression on the different classes of lipoproteins. FIGS. 1A and 1B (pre-treatment) show the lipoprotein profile of normal C57BL/6 mice, with most cholesterol contained in the HDL fraction, and low or undetectable VLDL and IDL/LDL fractions. Infusion of the control Ad.ΔE1 virus had virtually no effect on the lipoprotein profiles at earlier (FIG. 1A, pretreatment to day 3) or later (FIG. 1C, days 7 to 21) time points, consistent with the absence of changes in total plasma cholesterol and apoAI levels (Table 1). Plasma lipoproteins of SR-BI infused mice, although identical to control mice pre-infusion, showed a large decrease in HDL cholesterol on day 3 (FIG. 1B). This suggests that SR-BI overexpression in liver causes increased uptake of plasma HDL cholesterol, and thus lowers circulating HDL levels. This is consistent with the lower total plasma cholesterol levels on day 3 (Table 1). At later time points, SR-BI levels slowly declined, and HDL cholesterol slowly increased (FIG. 1D). In parallel, on days 7 and 10, an increase in both VLDL and IDL/LDL cholesterol were observed, suggesting either increased VLDL secretion by the liver, or a down-regulation of LDL receptors. These changes may occur as a result of increased cholesterol uptake by the liver through HDL-derived cholesterol taken up by SR-BI. The VLDL and IDL/LDL levels decreased to baseline levels by day 21, although HDL cholesterol remained below baseline, suggesting that SR-BI may still be active.

Figure 2:
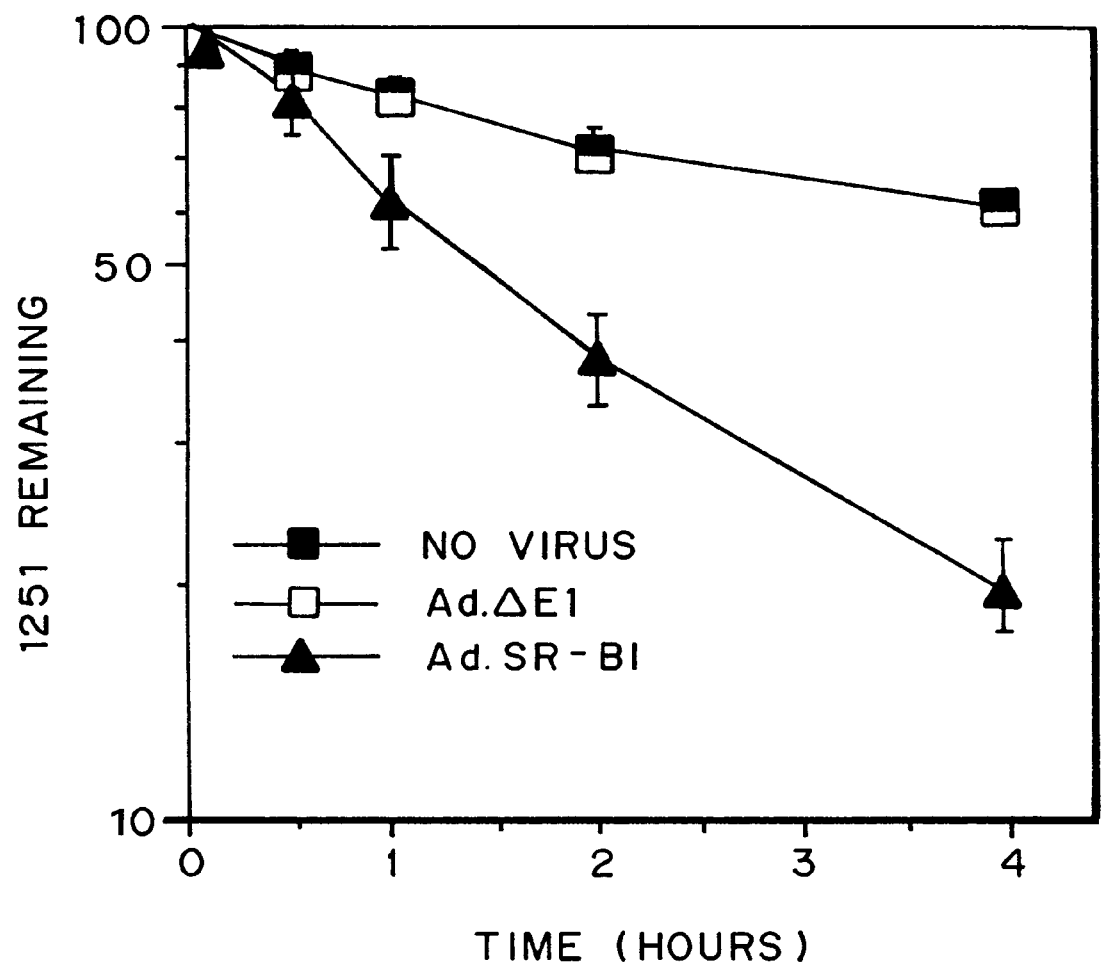
FIG. 2 is a graph of HDL turnover over time (hours) in untreated, normal mice (closed squares), control (Ad.ΔE1) (open squares) and transgenic mice (Ad.SR-BI) (closed triangles).

To examine the fate of the HDL particle, an HDL clearance study was performed. Mice were infused with either the control virus Ad.ΔE1, or with Ad.SR-BI. Five days following virus infusion, when transgene expression levels are maximal, mice were infused with $^{125}$I-labeled HDL, which is labeled in the protein portion (primarily apoAI). Plasma samples were obtained at various time points, and the amount of $^{125}$I remaining in the plasma was determined. FIG. 2 shows that mice overexpressing SR-BI (triangles) had a faster rate of HDL turnover than either uninfused (closed squares) or control virus infused mice (open squares). This suggests that the HDL particle itself may be degraded following SR-BI-mediated uptake of HDL-derived cholesterol.

Unlike LDL cholesterol, HDL-derived cholesterol is believed to be preferentially excreted in bile. Thus, bile excreted from SR-BI overexpressing mice was analyzed for cholesterol, bile salt, and phospholipid content. Four days following infusion of control virus (Ad.ΔE1) or Ad.SR-BI, mice were anesthetized, bile ducts were cannulated, and bile collected for approximately 1 hour to obtain at least 0.1 ml of bile. Table 2 shows that bile from SR-BI mice contained approximately 2-fold more free cholesterol than control mice, while bile salts and phospholipid did not change. This demonstrates that one consequence of increased hepatic uptake of HDL cholesterol is increased cholesterol excretion in bile.

TABLE 2

Bile cholesterol levels.

| | Cholesterol (mM) | Bile salts (mM) | Phospholipid (mM) |
| --- | --- | --- | --- |
| no virus | 0.490 ± 0.138 | 20.5 ± 6.4 | 3.95 ± 1.01 |
| Ad.ΔE1 | 0.572 ± 0.132 | 23.2 ± 10.7 | 3.64 ± 1.24 |
| Ad.SR-BI | 1.149 ± 0.358[a] | 19.7 ± 5.9 | 4.72 ± 1.48 | n = 8 to 13 for each group

[a], $p << 0.0005$ compared to both no virus and Ad.ΔE1 controls

As an indirect marker of HDL-cholesterol transfer to hepatocytes, mice were injected with DiI-HDL, which are labeled with a fluorescent lipid (DiI). These particles have previously been shown in cell culture to transfer the DiI at a rate comparable to the rate of transfer of the cholesterol ester. Five days after virus infusion, mice were injected with 40 μg of DiI-HDL. Two hours later, mice were anesthetized, perfused, and liver tissues were taken. Fresh-frozen sections of liver from SR-BI overexpressing mice stained strongly with the anti-SR-BI antibody and had high DiI content, as viewed under the fluorescent microscope. In contrast, control mice had low DiI content. Furthermore, in several mice, DiI transfer to bile was measured. Bile from control mice (n=7) had fluorescence intensity ranging from 0.11 to 0.19 (relative units). In contrast, bile from the two SR-BI overexpressing mice in this experiment had fluorescence intensities of 1.13 and 0.93.

Taken together, these data show that hepatic SR-BI overexpression increases uptake of HDL-derived lipid into the liver, and that in turn some of the cholesterol can be excreted in the bile. These data further suggest that inhibition of SR-BI should increase HDL cholesterol blood levels. This is expected to provide a mechanism for decreasing cholesterol secretion into the gall bladder and therefore inhibit gallstone formation.

Modifications and variations of the methods and materials described herein will be obvious to those skilled in the art and are intended to be encompassed by the following claims. The teachings of the references cited herein are specifically incorporated herein.

We claim:

1. A method for selectively altering transport of lipid, cholesterol, lipoprotein or component thereof into and out of mammalian cells in an amount effective to alter plasma cholesterol comprising administering a composition in an amount effective to alter expression or activity of SR-BI and thus alter the rate of clearance of the protein component of HDL as compared to the cholesterol ester component of the HDL.

2. The method of claim 1 wherein transport of lipid, cholesterol, lipoprotein or component thereof into liver, steroidogenic tissues, epithelial cells in the gastrointestinal tract, bile canniculi, bile ducts, or other body compartments is altered.

3. The method of claim 2 wherein transport of lipid, cholesterol, lipoprotein or component of the lipoprotein into steroidogenic tissues is inhibited or stimulated by administration of a hormone inhibiting or stimulating SR-BI expression.

4. The method of claim 3 wherein the hormone is an estrogen.

5. The method of claim 2 wherein transport of lipid, cholesterol, lipoprotein or component of the lipoprotein into the bile ducts is inhibited by administering a compound inhibiting transport of the cholesterol by SR-BI.

6. The method of claim 1 wherein transport of lipid, cholesterol, lipoprotein or component of the lipoprotein is inhibited or stimulated by administering a compound which binds to a regulatory nucleic acid sequence and therefore inhibits or increases expression of SR-BI.

7. The method of claim 1 wherein transport of lipid, cholesterol, lipoprotein or component of the lipoprotein is inhibited by administering a compound which binds to the SR-BI and prevents binding of lipid, cholesterol, lipoprotein or component of the lipoprotein to the receptor.

8. The method of claim 1 comprising administering a compound which induces expression of SR-BI to increase transport of lipid, cholesterol, lipoprotein or component of the lipoprotein.

9. The method of claim 8 wherein the compound is a viral vector encoding SR-BI.

10. The method of claim 9 wherein the viral vector is an adenoviral vector.

* * * * *

UNITED STATES PATENT AND TRADEMARK OFFICE
CERTIFICATE OF CORRECTION

PATENT NO. : 5,962,322 Page 1 of 1
APPLICATION NO. : 08/749907
DATED : October 5, 1999
INVENTOR(S) : Kozarsky et al.

It is certified that error appears in the above-identified patent and that said Letters Patent is hereby corrected as shown below:

In column 31 line 27, after "composition" insert --of polynucleotides or small molecules or peptides--.

Signed and Sealed this

First Day of July, 2008

JON W. DUDAS
*Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 1788 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (ix) FEATURE:
    (A) NAME/KEY: misc_feature
    (B) LOCATION: 156..1683
    (D) OTHER INFORMATION: /function= "Nucleotides 156 through
        1683 encode the amino acid sequence for the Hamster
        Scavenger Receptor Class B-I."

(xi) SEQUENCE DESCRIPTION: SEQ ID NO:1:

```
GCCACCTGCA GGGCTACTGC TGCTCCGGCC ACTGCCTGAG ACTCACCTTG CTGGAACGTG      60

AGCCTCGGCT TCTGTCATCT CTGTGGCCTC TGTCGCTTCT GTCGCTGTCC CCCTTCAGTC     120

CCTGAGCCCC GCGAGCCCGG GCCGCACACG CGGACATGGC CGGCAGCGCC AGGGCGCGCT     180

GGGTGGCGGT GGGGCTGGGC GTCGTGGGGC TGCTGTGCGC TGTGCTCGGT GTGGTTATGA     240

TCCTCGTGAT GCCCTCGCTC ATCAAACAGC AGGTACTGAA GAATGTCCGC ATAGACCCCA     300

GCAGCCTGTC CTTTGCAATG TGGAAGGAGA TCCCTGTACC CTTCTACTTG TCCGTCTACT     360

TCTTCGAGGT GGTCAATCCC AGCGAGATCC TAAAGGGTGA GAAGCCAGTA GTGCGGGAGC     420

GTGGACCCTA TGTCTACAGG GAATTCAGAC ATAAGGCCAA CATCACCTTC AATGACAATG     480

ATACTGTGTC CTTTGTGGAG CACCGCAGCC TCCATTTCCA GCCGGACAGG TCCCACGGCT     540

CTGAGAGTGA CTACATTATA CTGCCTAACA TTCTGGTCTT GGGGGGCGCA GTAATGATGG     600

AGAGCAAGTC TGCAGGCCTG AAGCTGATGA TGACCTTGGG GCTGGCCACC TTGGGCCAGC     660

GTGCCTTTAT GAACCGAACA GTTGGTGAGA TCCTGTGGGG CTATGAGGAT CCCTTCGTGA     720

ATTTTATCAA CAAATACTTA CCAGACATGT TCCCCATCAA GGGCAAGTTC GGCCTGTTTG     780

TTGAGATGAA CAACTCAGAC TCTGGGCTCT TCACTGTGTT CACGGGCGTC CAGAACTTCA     840

GCAAGATCCA CCTGGTGGAC AGATGGAATG GGCTCAGCAA GGTCAACTAC TGGCATTCAG     900

AGCAGTGCAA CATGATCAAT GGCACTTCCG GGCAGATGTG GCACCATTC ATGACACCCC      960

AGTCCTCGCT GGAATTCTTC AGTCCGGAAG CCTGCAGGTC TATGAAGCTC ACCTACCATG    1020

ATTCAGGGGT GTTTGAAGGC ATCCCCACCT ATCGCTTCAC AGCCCCTAAA ACTTTGTTTG    1080

CCAATGGGTC TGTTTACCCA CCCAATGAAG GTTTCTGCCC GTGCCTTGAA TCCGGCATTC    1140

AAAATGTCAG CACTTGCAGG TTTGGTGCAC CCCTGTTTCT GTCACACCCT CACTTCTACA    1200

ATGCAGACCC TGTGCTATCA GAAGCCGTTC TGGGTCTGAA CCCTGACCCA AGGGAGCATT    1260

CTTTGTTCCT TGACATCCAT CCGGTCACTG GGATCCCCAT GAACTGTTCT GTGAAGTTGC    1320

AGATAAGCCT CTACATCAAA GCTGTCAAGG GCATTGGGCA AACAGGGAAG ATCGAGCCCG    1380

TGGTCCTCCC ATTGCTGTGG TTTGAGCAGA GCGGTGCCAT GGGCGGCGAG CCCCTGAACA    1440

CGTTCTACAC GCAGCTGGTG CTGATGCCCC AGGTACTTCA GTATGTGCAG TATGTGCTGC    1500

TGGGGCTGGG CGGCCTCCTG CTGCTGGTGC CCGTCATCTA CCAGTTGCGC AGCCAGGAGA    1560

AATGCTTTTT ATTTTGGAGT GGTAGTAAAA AGGGCTCGCA GGATAAGGAG GCCATTCAGG    1620

CCTACTCTGA GTCTCTGATG TCACCAGCTG CCAAGGGCAC GGTGCTGCAA GAAGCCAAGC    1680

TGTAGGGTCC CAAAGACACC ACGAGCCCCC CCAACCTGAT AGCTTGGTCA GACCAGCCAT    1740
```

```
CCAGCCCCTA CACCCCGCTT CTTGAGGACT CTCTCAGCGG ACAGTCGC                  1788
```

(2) INFORMATION FOR SEQ ID NO:2:

(i) SEQUENCE CHARACTERISTICS:
        (A) LENGTH: 509 amino acids
        (B) TYPE: amino acid
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: misc_feature
        (B) LOCATION: 1..509
        (D) OTHER INFORMATION: /function= "Amino acid sequence for the
            Hamster Scavenger Receptor Class B-I."

(ix) FEATURE:
        (A) NAME/KEY: Domain
        (B) LOCATION: 9..32
        (D) OTHER INFORMATION: /note= "Putative transmembrane domain."

(ix) FEATURE:
        (A) NAME/KEY: Domain
        (B) LOCATION: 440..464
        (D) OTHER INFORMATION: /note= "Putative transmembrane domain."

(ix) FEATURE:
        (A) NAME/KEY: Modified-site
        (B) LOCATION: 1..385
        (D) OTHER INFORMATION: /note= "Positions 102-104, 108-110,
            173-175, 212-214, 227-229, 255-257, 310-312, 330-332 and
            383-385 represent potential N-linked glycosylation
            sites."

(ix) FEATURE:
        (A) NAME/KEY: Modified-site
        (B) LOCATION: 21..470
        (D) OTHER INFORMATION: /note= "The cysteines at positions 21,
            251, 280, 321, 323, 334, 384 and 470 represent potential
            disulfide linkages."

(xi) SEQUENCE DESCRIPTION: SEQ ID NO:2:

```
Met Gly Gly Ser Ala Arg Ala Arg Trp Val Ala Val Gly Leu Gly Val
1               5                   10                  15

Val Gly Leu Leu Cys Ala Val Leu Gly Val Val Met Ile Leu Val Met
                20                  25                  30

Pro Ser Leu Ile Lys Gln Gln Val Leu Lys Asn Val Arg Ile Asp Pro
            35                  40                  45

Ser Ser Leu Ser Phe Ala Met Trp Lys Glu Ile Pro Val Pro Phe Tyr
50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
                100                 105                 110

Phe Val Glu His Arg Ser Leu His Phe Gln Pro Asp Arg Ser His Gly
            115                 120                 125

Ser Glu Ser Asp Tyr Ile Ile Leu Pro Asn Ile Leu Val Leu Gly Gly
            130                 135                 140

Ala Val Met Met Glu Ser Lys Ser Ala Gly Leu Lys Leu Met Met Thr
145                 150                 155                 160

Leu Gly Leu Ala Thr Leu Gly Gln Arg Ala Phe Met Asn Arg Thr Val
```

```
                165                 170                 175
Gly Glu Ile Leu Trp Gly Tyr Glu Asp Pro Phe Val Asn Phe Ile Asn
            180                 185                 190
Lys Tyr Leu Pro Asp Met Phe Pro Ile Lys Gly Lys Phe Gly Leu Phe
        195                 200                 205
Val Glu Met Asn Asn Ser Asp Ser Gly Leu Phe Thr Val Phe Thr Gly
    210                 215                 220
Val Gln Asn Phe Ser Lys Ile His Leu Val Asp Arg Trp Asn Gly Leu
225                 230                 235                 240
Ser Lys Val Asn Tyr Trp His Ser Glu Gln Cys Asn Met Ile Asn Gly
                245                 250                 255
Thr Ser Gly Gln Met Trp Ala Pro Phe Met Thr Pro Gln Ser Ser Leu
            260                 265                 270
Glu Phe Phe Ser Pro Glu Ala Cys Arg Ser Met Lys Leu Thr Tyr His
        275                 280                 285
Asp Ser Gly Val Phe Glu Gly Ile Pro Thr Tyr Arg Phe Thr Ala Pro
    290                 295                 300
Lys Thr Leu Phe Ala Asn Gly Ser Val Tyr Pro Pro Asn Glu Gly Phe
305                 310                 315                 320
Cys Pro Cys Leu Glu Ser Gly Ile Gln Asn Val Ser Thr Cys Arg Phe
                325                 330                 335
Gly Ala Pro Leu Phe Leu Ser His Pro His Phe Tyr Asn Ala Asp Pro
            340                 345                 350
Val Leu Ser Glu Ala Val Leu Gly Leu Asn Pro Asp Pro Arg Glu His
        355                 360                 365
Ser Leu Phe Leu Asp Ile His Pro Val Thr Gly Ile Pro Met Asn Cys
    370                 375                 380
Ser Val Lys Leu Gln Ile Ser Leu Tyr Ile Lys Ala Val Lys Gly Ile
385                 390                 395                 400
Gly Gln Thr Gly Lys Ile Glu Pro Val Val Leu Pro Leu Leu Trp Phe
                405                 410                 415
Glu Gln Ser Gly Ala Met Gly Gly Glu Pro Leu Asn Thr Phe Tyr Thr
            420                 425                 430
Gln Leu Val Leu Met Pro Gln Val Leu Gln Tyr Val Gln Tyr Val Leu
        435                 440                 445
Leu Gly Leu Gly Gly Leu Leu Leu Val Pro Val Ile Tyr Gln Leu
    450                 455                 460
Arg Ser Gln Glu Lys Cys Phe Leu Phe Trp Ser Gly Ser Lys Lys Gly
465                 470                 475                 480
Ser Gln Asp Lys Glu Ala Ile Gln Ala Tyr Ser Glu Ser Leu Met Ser
                485                 490                 495
Pro Ala Ala Lys Gly Thr Val Leu Gln Glu Ala Lys Leu
            500                 505

(2) INFORMATION FOR SEQ ID NO:3:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO
```

(ix) FEATURE:
    (A) NAME/KEY: CDS
    (B) LOCATION: 51..1577
    (D) OTHER INFORMATION: /Function = "Nucleotides 51 through
       1577 encode the amino acid sequence for the murine
       Scavenger Receptor Class BI."

(xi) SEQUENCE DESCRIPTION: SEQ ID NO:3:

```
CCGTCTCCTT CAGGTCCTGA GCCCCGAGAG CCCCTTCCGC GCACGCGGAC ATG GGC        56
                                                     Met Gly
                                                       1

GGC AGC TCC AGG GCG CGC TGG GTG GCC TTG GGG TTG GGC GCC CTG GGG      104
Gly Ser Ser Arg Ala Arg Trp Val Ala Leu Gly Leu Gly Ala Leu Gly
          5                  10                  15

CTG CTG TTT GCT GCG CTC GGC GTT GTC ATG ATC CTC ATG GTG CCC TCC      152
Leu Leu Phe Ala Ala Leu Gly Val Val Met Ile Leu Met Val Pro Ser
 20                  25                  30

CTC ATC AAG CAG CAG GTG CTC AAG AAT GTC CGC ATA GAC CCG AGC AGC      200
Leu Ile Lys Gln Gln Val Leu Lys Asn Val Arg Ile Asp Pro Ser Ser
 35                  40                  45                  50

CTG TCC TTC GGG ATG TGG AAG GAG ATC CCC GTC CCT TTC TAC TTG TCT      248
Leu Ser Phe Gly Met Trp Lys Glu Ile Pro Val Pro Phe Tyr Leu Ser
             55                  60                  65

GTC TAC TTC TTC GAA GTG GTC AAC CCA AAC GAG GTC CTC AAC GGC CAG      296
Val Tyr Phe Phe Glu Val Val Asn Pro Asn Glu Val Leu Asn Gly Gln
         70                  75                  80

AAG CCA GTA GTC CGG GAG CGT GGA CCC TAT GTC TAC AGG GAG TTC AGA      344
Lys Pro Val Val Arg Glu Arg Gly Pro Tyr Val Tyr Arg Glu Phe Arg
             85                  90                  95

CAA AAG GTC AAC ATC ACC TTC AAT GAC AAC GAC ACC GTG TCC TTC GTG      392
Gln Lys Val Asn Ile Thr Phe Asn Asp Asn Asp Thr Val Ser Phe Val
100                 105                 110

GAG AAC CGC AGC CTC CAT TTC CAG CCT GAC AAG TCG CAT GGC TCA GAG      440
Glu Asn Arg Ser Leu His Phe Gln Pro Asp Lys Ser His Gly Ser Glu
115                 120                 125                 130

AGT GAC TAC ATT GTA CTG CCT AAC ATC TTG GTC CTG GGG GGC TCG ATA      488
Ser Asp Tyr Ile Val Leu Pro Asn Ile Leu Val Leu Gly Gly Ser Ile
                135                 140                 145

TTG ATG GAG AGC AAG CCT GTG AGC CTG AAG CTG ATG ATG ACC TTG GCG      536
Leu Met Glu Ser Lys Pro Val Ser Leu Lys Leu Met Met Thr Leu Ala
                150                 155                 160

CTG GTC ACC ATG GGC CAG CGT GCT TTT ATG AAC CGC ACA GTT GGT GAG      584
Leu Val Thr Met Gly Gln Arg Ala Phe Met Asn Arg Thr Val Gly Glu
            165                 170                 175

ATC CTG TGG GGC TAT GAC GAT CCC TTC GTG CAT TTT CTC AAC ACG TAC      632
Ile Leu Trp Gly Tyr Asp Asp Pro Phe Val His Phe Leu Asn Thr Tyr
            180                 185                 190

CTC CCA GAC ATG CTT CCC ATA AAG GGC AAA TTT GGC CTG TTT GTT GGG      680
Leu Pro Asp Met Leu Pro Ile Lys Gly Lys Phe Gly Leu Phe Val Gly
195                 200                 205                 210

ATG AAC AAC TCG AAT TCT GGG GTC TTC ACT GTC TTC ACG GGC GTC CAG      728
Met Asn Asn Ser Asn Ser Gly Val Phe Thr Val Phe Thr Gly Val Gln
                215                 220                 225

AAT TTC AGC AGG ATC CAT CTG GTG GAC AAA TGG AAC GGA CTC AGC AAG      776
Asn Phe Ser Arg Ile His Leu Val Asp Lys Trp Asn Gly Leu Ser Lys
            230                 235                 240

ATC GAT TAT TGG CAT TCA GAG CAG TGT AAC ATG ATC AAT GGG ACT TCC      824
Ile Asp Tyr Trp His Ser Glu Gln Cys Asn Met Ile Asn Gly Thr Ser
            245                 250                 255

GGG CAG ATG TGG GCA CCC TTT ATG ACA CCC GAA TCC TCG CTG GAA TTC      872
Gly Gln Met Trp Ala Pro Phe Met Thr Pro Glu Ser Ser Leu Glu Phe
        260                 265                 270
```

```
TTC AGC CCG GAG GCA TGC AGG TCC ATG AAG CTG ACC TAC AAC GAA TCA        920
Phe Ser Pro Glu Ala Cys Arg Ser Met Lys Leu Thr Tyr Asn Glu Ser
275                 280                 285                 290

AGG GTG TTT GAA GGC ATT CCC ACG TAT CGC TTC ACG GCC CCC GAT ACT        968
Arg Val Phe Glu Gly Ile Pro Thr Tyr Arg Phe Thr Ala Pro Asp Thr
                    295                 300                 305

CTG TTT GCC AAC GGG TCC GTC TAC CCA CCC AAC GAA GGC TTC TGC CCA       1016
Leu Phe Ala Asn Gly Ser Val Tyr Pro Pro Asn Glu Gly Phe Cys Pro
                310                 315                 320

TGC CGA GAG TCT GGC ATT CAG AAT GTC AGC ACC TGC AGG TTT GGT GCG       1064
Cys Arg Glu Ser Gly Ile Gln Asn Val Ser Thr Cys Arg Phe Gly Ala
            325                 330                 335

CCT CTG TTT CTC TCC CAC CCC CAC TTT TAC AAC GCC GAC CCT GTG TTG       1112
Pro Leu Phe Leu Ser His Pro His Phe Tyr Asn Ala Asp Pro Val Leu
        340                 345                 350

TCA GAA GCT GTT CTT GGT CTG AAC CCT AAC CCA AAG GAG CAT TCC TTG       1160
Ser Glu Ala Val Leu Gly Leu Asn Pro Asn Pro Lys Glu His Ser Leu
355                 360                 365                 370

TTC CTA GAC ATC CAT CCG GTC ACT GGG ATC CCC ATG AAC TGT TCT GTG       1208
Phe Leu Asp Ile His Pro Val Thr Gly Ile Pro Met Asn Cys Ser Val
                    375                 380                 385

AAG ATG CAG CTG AGC CTC TAC ATC AAA TCT GTC AAG GGC ATC GGG CAA       1256
Lys Met Gln Leu Ser Leu Tyr Ile Lys Ser Val Lys Gly Ile Gly Gln
                390                 395                 400

ACA GGG AAG ATC GAG CCA GTA GTT CTG CCG TTG CTG TGG TTC GAA CAG       1304
Thr Gly Lys Ile Glu Pro Val Val Leu Pro Leu Leu Trp Phe Glu Gln
            405                 410                 415

AGC GGA GCA ATG GGT GGC AAG CCC CTG AGC ACG TTC TAC ACG CAG CTG       1352
Ser Gly Ala Met Gly Gly Lys Pro Leu Ser Thr Phe Tyr Thr Gln Leu
        420                 425                 430

GTG CTG ATG CCC CAG GTT CTT CAC TAC GCG CAG TAT GTG CTG CTG GGG       1400
Val Leu Met Pro Gln Val Leu His Tyr Ala Gln Tyr Val Leu Leu Gly
435                 440                 445                 450

CTT GGA GGC CTC CTG TTG CTG GTG CCC ATC ATC TGC CAA CTG CGC AGC       1448
Leu Gly Gly Leu Leu Leu Leu Val Pro Ile Ile Cys Gln Leu Arg Ser
                    455                 460                 465

CAG GAG AAA TGC TTT TTG TTT TGG AGT GGT AGT AAA AAG GGC TCC CAG       1496
Gln Glu Lys Cys Phe Leu Phe Trp Ser Gly Ser Lys Lys Gly Ser Gln
                470                 475                 480

GAT AAG GAG GCC ATT CAG GCC TAC TCT GAG TCC CTG ATG TCA CCA GCT       1544
Asp Lys Glu Ala Ile Gln Ala Tyr Ser Glu Ser Leu Met Ser Pro Ala
            485                 490                 495

GCC AAG GGC ACG GTG CTG CAA GAA GCC AAG CTA TAGGGTCCTG AAGACACTAT     1597
Ala Lys Gly Thr Val Leu Gln Glu Ala Lys Leu
        500                 505

AAGCCCCCCA AACCTGATAG CTTGGTCAGA CCAGCCACCC AGTCCCTACA CCCCGCTTCT     1657

TGAGGACTCT CTCAGCGGAC AGCCCACCAG TGCCATGGCC TGAGCCCCCA GATGTCACAC     1717

CTGTCCGCAC GCACGGCACA TGGATGCCCA CGCATGTGCA AAAACAACTC AGGGACCAGG     1777

GACAGACC                                                             1785

(2) INFORMATION FOR SEQ ID NO:4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (ix) FEATURE:
```

(A) NAME/KEY: misc. feature
(B) LOCATION: 1..509
(D) OTHER INFORMATION: /Function = "Amino acid sequence for the murine Scavenger Receptor Class BI."

(xi) SEQUENCE DESCRIPTION: SEQ ID NO:4:

Met Gly Gly Ser Ser Arg Ala Arg Trp Val Ala Leu Gly Leu Gly Ala
1               5                   10                  15

Leu Gly Leu Leu Phe Ala Ala Leu Gly Val Val Met Ile Leu Met Val
            20                  25                  30

Pro Ser Leu Ile Lys Gln Gln Val Leu Lys Asn Val Arg Ile Asp Pro
        35                  40                  45

Ser Ser Leu Ser Phe Gly Met Trp Lys Glu Ile Pro Val Pro Phe Tyr
    50                  55                  60

Leu Ser Val Tyr Phe Phe Glu Val Val Asn Pro Asn Glu Val Leu Asn
65                  70                  75                  80

Gly Gln Lys Pro Val Val Arg Glu Arg Gly Pro Tyr Val Tyr Arg Glu
                85                  90                  95

Phe Arg Gln Lys Val Asn Ile Thr Phe Asn Asp Asn Asp Thr Val Ser
            100                 105                 110

Phe Val Glu Asn Arg Ser Leu His Phe Gln Pro Asp Lys Ser His Gly
        115                 120                 125

Ser Glu Ser Asp Tyr Ile Val Leu Pro Asn Ile Leu Val Leu Gly Gly
    130                 135                 140

Ser Ile Leu Met Glu Ser Lys Pro Val Ser Leu Lys Leu Met Met Thr
145                 150                 155                 160

Leu Ala Leu Val Thr Met Gly Gln Arg Ala Phe Met Asn Arg Thr Val
                165                 170                 175

Gly Glu Ile Leu Trp Gly Tyr Asp Asp Pro Phe Val His Phe Leu Asn
            180                 185                 190

Thr Tyr Leu Pro Asp Met Leu Pro Ile Lys Gly Lys Phe Gly Leu Phe
        195                 200                 205

Val Gly Met Asn Asn Ser Asn Ser Gly Val Phe Thr Val Phe Thr Gly
    210                 215                 220

Val Gln Asn Phe Ser Arg Ile His Leu Val Asp Lys Trp Asn Gly Leu
225                 230                 235                 240

Ser Lys Ile Asp Tyr Trp His Ser Glu Gln Cys Asn Met Ile Asn Gly
                245                 250                 255

Thr Ser Gly Gln Met Trp Ala Pro Phe Met Thr Pro Glu Ser Ser Leu
            260                 265                 270

Glu Phe Phe Ser Pro Glu Ala Cys Arg Ser Met Lys Leu Thr Tyr Asn
        275                 280                 285

Glu Ser Arg Val Phe Glu Gly Ile Pro Thr Tyr Arg Phe Thr Ala Pro
    290                 295                 300

Asp Thr Leu Phe Ala Asn Gly Ser Val Tyr Pro Pro Asn Glu Gly Phe
305                 310                 315                 320

Cys Pro Cys Arg Glu Ser Gly Ile Gln Asn Val Ser Thr Cys Arg Phe
                325                 330                 335

Gly Ala Pro Leu Phe Leu Ser His Pro His Phe Tyr Asn Ala Asp Pro
            340                 345                 350

Val Leu Ser Glu Ala Val Leu Gly Leu Asn Pro Asn Pro Lys Glu His
        355                 360                 365

Ser Leu Phe Leu Asp Ile His Pro Val Thr Gly Ile Pro Met Asn Cys
    370                 375                 380

Ser Val Lys Met Gln Leu Ser Leu Tyr Ile Lys Ser Val Lys Gly Ile

-continued

| 385 | | | | | 390 | | | | | 395 | | | | | 400 |
|---|---|---|---|---|---|---|---|---|---|---|---|---|---|---|---|
| Gly | Gln | Thr | Gly | Lys | Ile | Glu | Pro | Val | Val | Leu | Pro | Leu | Leu | Trp | Phe |
| | | | | 405 | | | | | 410 | | | | | 415 | |
| Glu | Gln | Ser | Gly | Ala | Met | Gly | Gly | Lys | Pro | Leu | Ser | Thr | Phe | Tyr | Thr |
| | | | 420 | | | | | 425 | | | | | 430 | | |
| Gln | Leu | Val | Leu | Met | Pro | Gln | Val | Leu | His | Tyr | Ala | Gln | Tyr | Val | Leu |
| | | 435 | | | | | 440 | | | | | 445 | | | |
| Leu | Gly | Leu | Gly | Gly | Leu | Leu | Leu | Val | Pro | Ile | Ile | Cys | Gln | Leu | |
| | 450 | | | | | 455 | | | | | 460 | | | | |
| Arg | Ser | Gln | Glu | Lys | Cys | Phe | Leu | Phe | Trp | Ser | Gly | Ser | Lys | Lys | Gly |
| 465 | | | | | 470 | | | | | 475 | | | | | 480 |
| Ser | Gln | Asp | Lys | Glu | Ala | Ile | Gln | Ala | Tyr | Ser | Glu | Ser | Leu | Met | Ser |
| | | | 485 | | | | | 490 | | | | | 495 | | |
| Pro | Ala | Ala | Lys | Gly | Thr | Val | Leu | Gln | Glu | Ala | Lys | Leu | | | |
| | | | 500 | | | | | 505 | | | | | | | |